(12) United States Patent
Erikson

(10) Patent No.: US 6,752,763 B2
(45) Date of Patent: *Jun. 22, 2004

(54) ORTHOGONALLY RECONFIGURABLE INTEGRATED MATRIX ACOUSTICAL ARRAY

(75) Inventor: Kenneth R. Erikson, Henniker, NH (US)

(73) Assignee: BAE Systems Information and Electronic Systems Integration INC, Nashua, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/308,246

(22) Filed: Dec. 2, 2002

(65) Prior Publication Data

US 2003/0120153 A1 Jun. 26, 2003

Related U.S. Application Data

(63) Continuation of application No. 09/969,438, filed on Oct. 2, 2001, now Pat. No. 6,524,254.
(60) Provisional application No. 60/299,634, filed on Jun. 20, 2001.

(51) Int. Cl.[7] .................................................. A61B 8/14
(52) U.S. Cl. ...................................................... 600/459
(58) Field of Search ................................ 600/440–459; 128/916; 73/625, 626; 367/7, 11, 130, 138, 105, 122; 310/328, 334, 335–348

(56) References Cited

U.S. PATENT DOCUMENTS

| 3,387,604 | A | 6/1968 | Erikson |
| 4,281,550 | A | 8/1981 | Erikson |
| 5,483,963 | A | 1/1996 | Butler et al. |
| 5,546,946 | A | 8/1996 | Souquet |
| 5,732,706 | A | 3/1998 | White et al. |
| 5,787,049 | A | 7/1998 | Bates |
| 5,913,785 | A | 6/1999 | Mason |
| 6,089,096 | A | 7/2000 | Alexandru |
| 6,111,816 | A | 8/2000 | Chiang et al. |
| 6,159,149 | A | 12/2000 | Erikson et al. |
| 6,183,419 | B1 | 2/2001 | Wildes |
| 6,222,948 | B1 | 4/2001 | Hossack et al. |
| 6,264,610 | B1 | 7/2001 | Zhu |
| 6,292,433 | B1 | 9/2001 | Gilbert et al. |
| 6,524,254 | B2 * | 2/2003 | Erikson ..................... 600/447 |
| 2001/0013510 | A1 | 8/2001 | Wiener-Avnear et al. |

OTHER PUBLICATIONS

C. Oakley et al., "Integrating Electronic Switching into an 896– element Piezoelectronic array to lower cable count", Paper presented at the 1999 U.S. Navy Workshop on Acoustic Transduction materials and Devices, The Penn State Conference Center, Apr. 1999.
Wells, P.N.T., *Physical Principles of Ultrasonic Diagnosis*, Academic Press, NY, NY, 1969.
Hinkelman, L. M. et al., "The effect of abdominal all morphology on ultrasonic pulse distortion", J. Acoust. Soc. Am. 104, 3635–3649 (1998).

(List continued on next page.)

Primary Examiner—Ali M. Imam
(74) Attorney, Agent, or Firm—Maine & Asmus

(57) ABSTRACT

A transducer probe has a fully populated, integrated, matrix array of acoustical transducers for ultrasound imaging. The transducer arrays include tiled subarrays of transducers which may be switched (e.g., in real-time) between vertical and horizontal modes, and may further be configured to perform a first level of transmit and receive beam forming functionality with either horizontal or vertical scanning. Example applications include medical imaging, materials testing, and sonar systems.

20 Claims, 25 Drawing Sheets

OTHER PUBLICATIONS

Horvat D. et al, "True Time–Delay Bandpass Beamforming", IEEE J. Oceanic Eng. 17: 185–192 (1992).

Powers, J.E. et al, "Ultrasound Phased Array Delay Lines based on Quadrature Sampling Techniques", IEEE Trans. Sonics and Ultrasonics, vol. SU–27, No. 6, pp. 287–294, Nov. 1980.

K.R. Erikson, "A 128×128 16k Ultrasonic transducer hybrid array," *Acoustical Imaging*, vol. 23, Ed. S. Lees & Terrari, Plenum Publ. NY, NY 1997.

K.R. Erikson, R Zuleeg, "Integrated Accoustic array", *Acoustical Holography*, vol. 7, Ed. L. Kesler, Plenum Publ. NY, NY 1977.

Selection guide for model US3 Cable Assemblies, Datasheet 102–sp–02–1023 Rev A Precision Interconect, Portland, OR 97224–7756, Aug. 2000.

W.A. Smith, B.A. Auld "Modeling 1–3 Composite Piezoeletrics: Thickness Mode Oscillations", IEEE Transactions on Ultrasonics, Ferroelectronics and Frequency Control, vol 38, No. 1, pp. 40–47, Jan. 1991.

P. Tournois et al. "A 128 ×4 1.5D curved linar array for medical imaging," Proc. IEEE 1995 Ultrasonics Symposium, pp. 1331–1336.

Erikson, Kenneth R., Imaging with a 2D Transducer Hybrid Array, Acoustical Imaging, 2000, vol. 24, Ed. H. Lee, Plenum Publishing Corp., New York, NY.

* cited by examiner

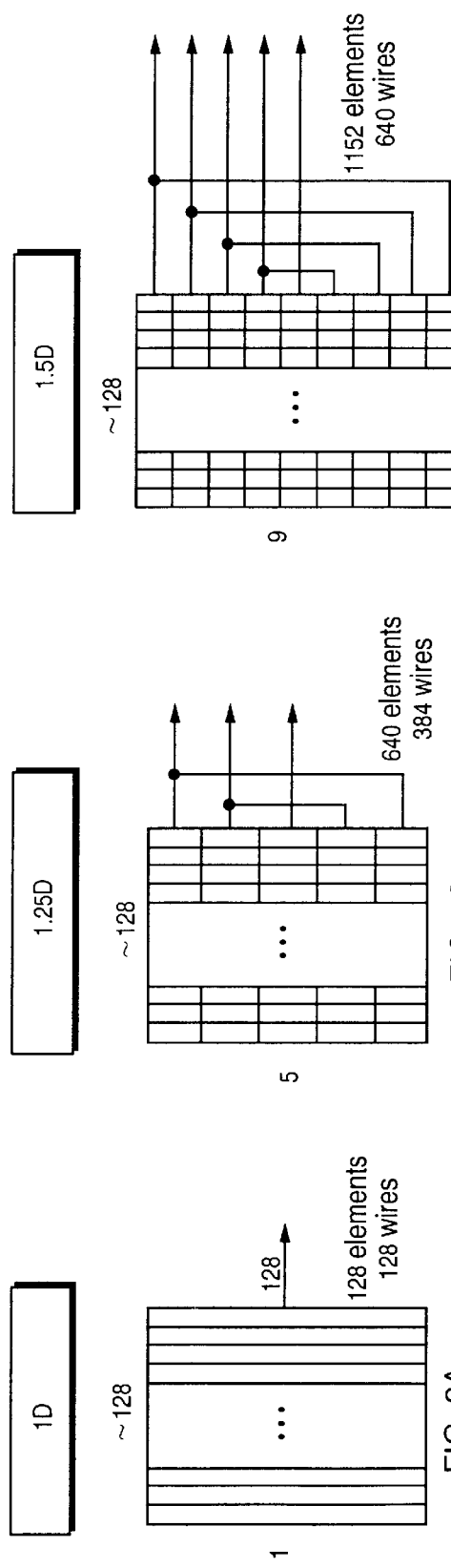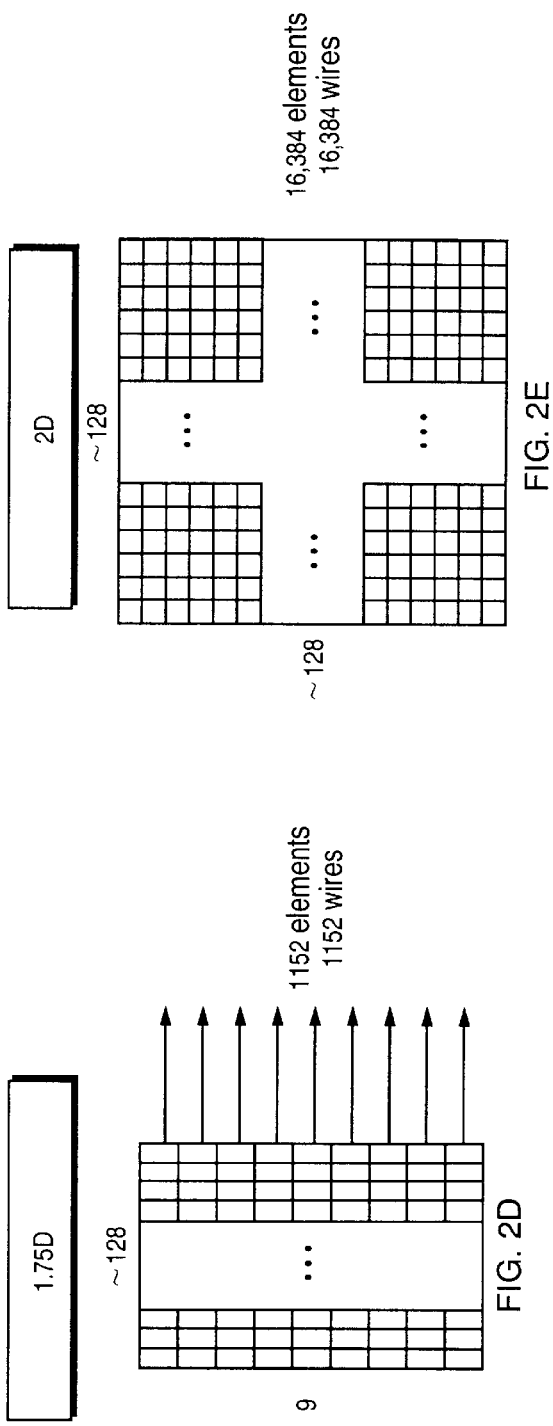

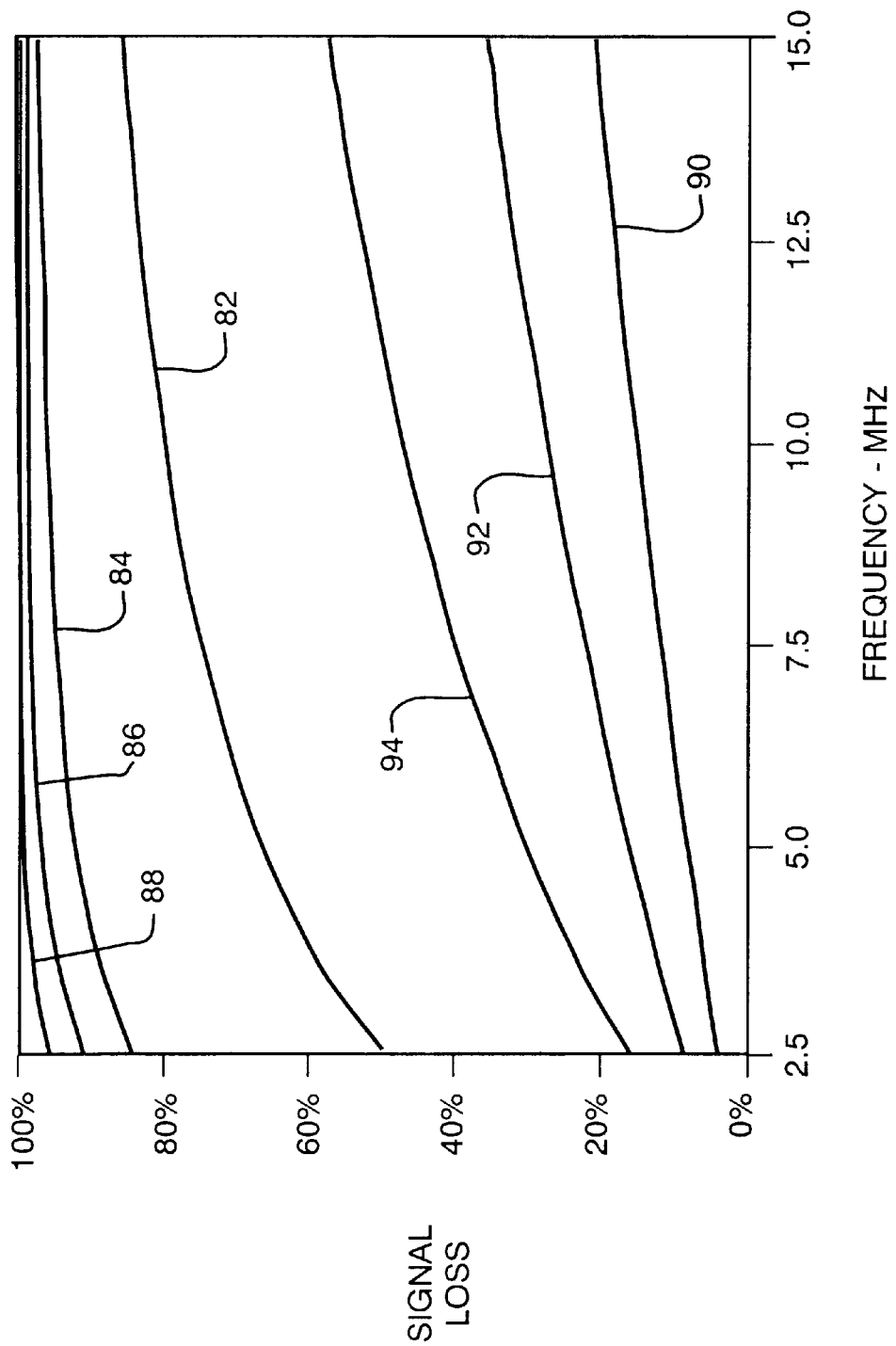

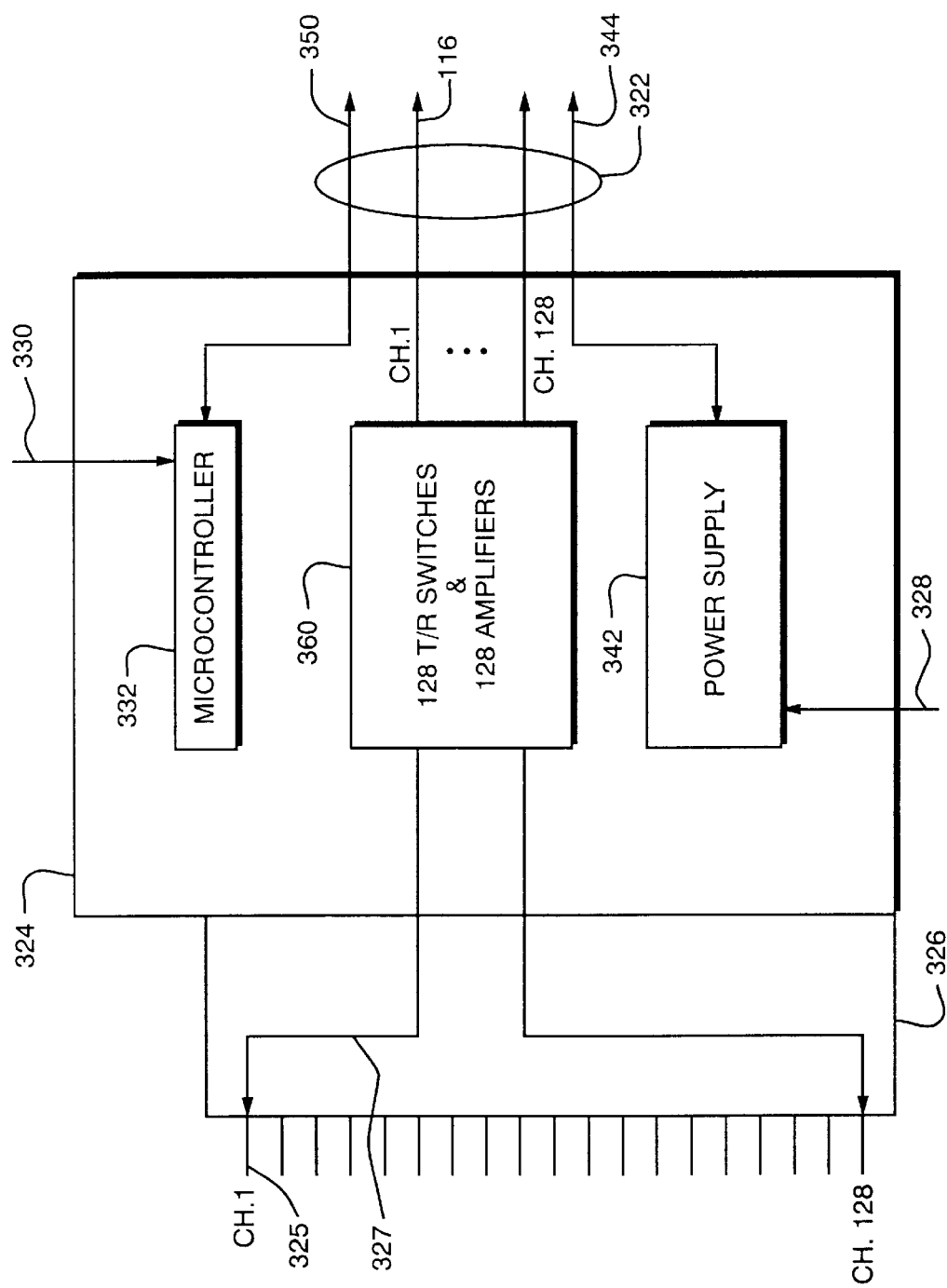

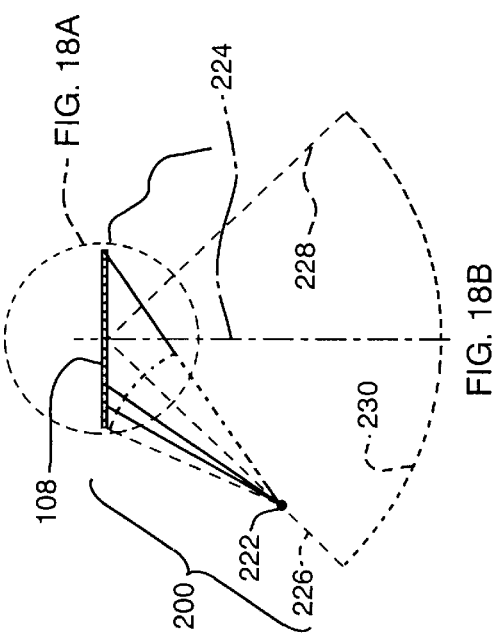
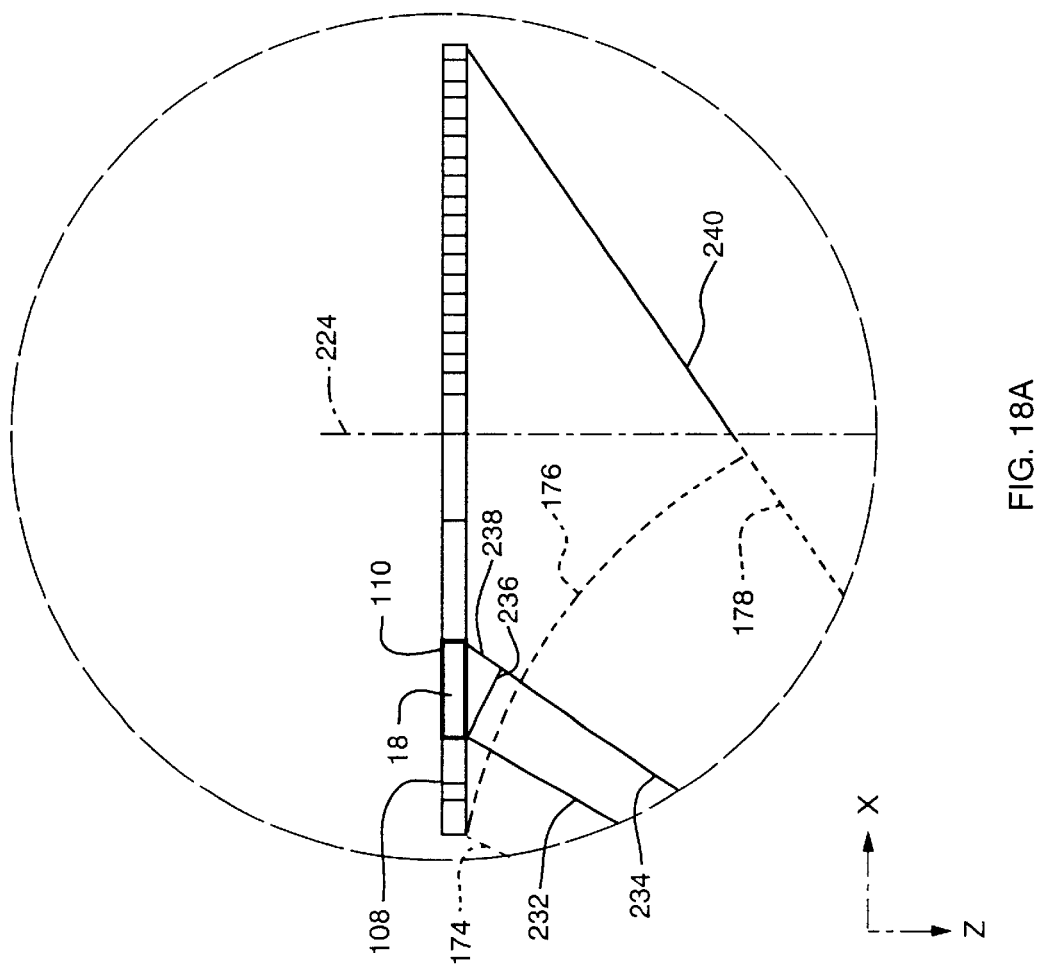
FIG. 18A
FIG. 18B

ORTHOGONALLY RECONFIGURABLE INTEGRATED MATRIX ACOUSTICAL ARRAY

RELATED APPLICATIONS

This application is a continuation of U.S. application Ser. No. 09/969,438, filed Oct. 02, 2001, now U.S. Pat. No. 6,524,254 which claims the benefit of U.S. Provisional Application No. 60/299,634, filed Jun. 20, 2001. Each of these applications is herein incorporated in its entirety by reference.

FIELD OF THE INVENTION

This invention relates to reconfigurable matrix acoustical arrays, and in particular to integrated matrix arrays configured for consolidating signal paths and orthogonally reconfigurable for operating orientation.

BACKGROUND OF THE INVENTION

Diagnostic ultrasound is an established and growing medical imaging modality. Currently one-dimensional ultrasound transducer arrays with up to 128 transducers are the standard in the industry. Separate coaxial cables are used to connect the transducers to the system electronics. Improved image quality requires the use of matrix (n by m) arrays with a thousand or more transducers. As transducer numbers increase and their dimensions grow smaller, limitations to present fabrication technologies arise. Cost, ergonomics, produce-ability and reliability are important issues. Signal loss due to the capacitance of the coax cables becomes a fundamental problem.

Medical ultrasound systems transmit a short pulse of ultrasound and receive echoes from structures within the body. The handheld probes are most often applied to the skin using a coupling gel. Specialty probes are available for endocavity, endoluminal and intraoperative scanning.

Almost all systems on the market today produce real-time, grayscale, B-scan images. Many systems include colorflow imaging.

Real-time images move as the operator moves the probe (or scanhead). Moving structures, such as the heart or a fetus, are shown on the video monitor.

Grayscale images depict the strength of echo signals from the body as shades of gray. Stronger signals generally are shown as bright white. Lower signals become gray and echo-free regions are black.

B-scans are cross-sectional or slice images.

Colorflow imaging adds a color overlay to the black and white image to depict blood flow.

Over the last 30 years, the major technical developments that have improved imaging or added diagnostic capability include:

Digital technology (late 70's to early 80's) provided image stability and improved signal processing;

Real-time imaging (late 70's to early 80's) provided quicker, easier imaging and functional information;

Electronically scanned linear arrays (late 70's to early 80's), including sequenced arrays and phased arrays, provided improved reliability;

Color-flow imaging (late-80's) opened up new cardiac and vascular applications;

Digital beamformers (early 90's) improved image quality;

Harmonic Imaging (late 90's) provided improved image quality particularly in difficult to image patients;

Coded-excitation Imaging (late 90's to present) permitted increased penetration allowing use of higher frequency ultrasound thereby improving image contrast;

Contrast agents (late 90's to present) offer improved functional information and better image quality.

3D (volumetric) imaging (late 90's to present) presents more easily interpreted images of surfaces such as the fetal face.

Referring to FIG. 1, there is illustrated a conventional linear transducer array ultrasound imaging system with probe shown in partial cross section, consisting of a system console [1], housing system electronics [2], to which can be connected the transducer probe assembly [4]. The probe assembly consists of the molded case [5] within which is housed an acoustic lens [6] over a 1 by 128 piezocomposite transducer array [8] with acoustical matching layers, an absorptive backing and structural support, and flexible printed circuit [10], connected to a 135 wire cable and mating connector for attaching to the system console. More details are provided below.

To form a typical sector (or wedge shaped) image, separate pulses are transmitted from each of the transducers of the array. The pulses are time-delayed with respect to each other so that the summation of the individual pulses is a maximum in the desired radial direction.

Upon reception, the echo signals received from structures within the body at each transducer are delayed with respect to each other to achieve a similar maximization along the same radial line. These signals are stored digitally.

To generate the next radial line in the image, the transmitter and receiver time delays are adjusted to change the direction of the maxima and the process is repeated. Images are thus built up line by line. Using digital storage (scan-conversion), they are converted to a conventional raster-scanned, gray-scale video image.

In general it is not required that the lines be contiguous, i.e. the selected line may come from one portion of the image on one pulse and a completely different portion of the image on the next pulse. The only requirement is that the image space is completely covered during the video image frame time. For example in a colorflow image overlayed on a grayscale image, the number of pulses allocated to the color portion may be several times that of the grayscale image.

When a pulse is transmitted by an array, transmitter time delays on each channel may also provide a focusing effect in addition to beam steering. On reception, the time delays may be adjusted in real-time as the pulse propagates into the body. This, provides a focusing effect that tracks the pulse. The dynamic, or tracking focus, thus sweeps out from the probe at the velocity of sound. Almost all ultrasound systems use dynamic focusing which provides greatly improved resolution and image quality in the scanning plane.

Referring to FIG. 2, one-dimensional (1 D, linear or 1×m) electronically scanned arrays are in widespread use today. Matrix arrays consisting of (n×m) transducers will be required in future systems to improve image quality. The various types of matrix arrays are the main topics of this discussion.

Referring to FIG. 2A, 1 D arrays may have as many as 128 transducers and either be flat or curved. All such arrays on the market today are connected to the system electronics through a bundle of coaxial cables. Beamformers in the system electronics adjust the time delays between channels to provide electronic sector scanning and focusing. High performance systems typically use all 128 transducers in their beamformers. Lower performance systems may use as few as 16 of the 128 transducers at any instant. The scanning function is performed by switching transducers into the aperture on the leading edge of the scan and switching out transducers at the trailing edge. Use of a curved array as discussed in Erikson, K. R, "Curved Array of Sequenced Ultrasound Transducers", U.S. Pat. No. 4,281,550, issued Aug. 4, 1981, produces a sector scan in these simpler, lower cost arrays.

Although one-dimensional arrays are almost universally accepted, these simple linear arrays have a basic limitation on image quality due to their fixed focus in the out-of-plane or elevation dimension. This leads to a slice thickness artifact. While the images appear to be infinitely thin slices, in fact they have finite thickness that changes along the depth dimension. This poor resolution can lead to many different artifacts. The most common is the filling-in of regions where echo levels are very low, with information from surrounding tissue.

Referring to FIG. 2B, 1.25 D arrays typically use a (128×3) or (128×5) matrix. They are connected to the system electronics through a similar bundle of coax cables as the 1D array. The same beamformers are also used for scanning and dynamic focusing. As the pulse propagates into the body, only the center transducer is initially selected for receiving the reflected signals. By switching in additional transducers as the pulse propagates, the receiving aperture is enlarged and the receiver is weakly focused. Moderate improvements in image quality are obtained.

Referring to FIG. 2C, 1.5 D arrays use a (128×n) matrix, with n typically an odd number, typically 5, 7 or 9. 1.5 D arrays use dynamic focusing in the plane perpendicular to the scanning plane. This produces optimal resolution in all dimensions, further reducing artifacts. The key difference between the 1.25 D and 1.5 D arrays is the active time-delay beamforming in both dimensions. The number of transducers in the elevation direction is often an odd number because transducers on each side of the beam axis are electrically connected together since they both have the same time delay for on-axis targets.

Referring to FIG. 2D, 1.75 D arrays are very similar to 1.5 D arrays with the exception that the transducers in the elevation direction are individually connected to the beamformer. Limited angular beamsteering can be performed in addition to dynamic focusing. Aberration correction is also possible with the 1.75 D array. These added capabilities are not present in a 1.5 D arrays, which only provides improved focusing for on-axis targets.

Referring to FIG. 2E, 2 D arrays are the most general type, with (n×m) transducers. Dynamic focusing as well as sector beamsteering in any arbitrary direction around the axis normal to plane of the array is possible. The angles are only limited by the constraints of the beam former, the number of transducers and their dimensions.

The improvements to ultrasound arrays discussed above were examples of technology push, i.e. new technology was developed and new applications followed. Improvements in transducer and array technology were either required or enabled many of the innovations.

One of the next major innovations is expected to be the use of matrix arrays, as opposed to the linear arrays currently in use. Although the 1.25 D array produces moderate improvement, the improved image quality of 1.5 D and 1.75 D arrays will make a quantum jump in resolution, image quality and freedom from artifacts.

Referring again to FIG. 1, fabrication techniques for 1 D probes (scanheads) are well established. FIG. 1 shows a typical probe in partial cross-section. The connector [3] that couples to the system electronics [2] of console [1] is a Cannon® DL 260 pin. The cable [5] has 135 coaxial cables bundled together in a sheath. Cable weight and flexibility are important ergonomic concerns for the operators who use the scanheads daily and for extended periods. Specifications of typical high performance cables are listed in Table 1. The scanhead end of the cable is terminated in a high density, fine pitch edge connector [7], (not shown).

TABLE 1

Typical Cable Parameters

| Coax Count | Impedance ohms | Capacitance pF/m | Cable O.D. in | Weight Oz./ft. |
|---|---|---|---|---|
| 102 | 50 | 101 | 0.275 | 0.9 |
| 102 | 75 | 53 | | 0.8 |
| 135 | 50 | 101 | 0.305 | 1.0 |
| 135 | 75 | 53 | | 0.9 |
| 200 | 50 | 101 | 0.345 | 1.4 |
| 200 | 75 | 53 | | 1.3 |

The multi-coax cable is electrically connected to the active piezocomposite array with a flexible printed circuit. One end of this flex circuit plugs into connector [7] and the other end is soldered or bonded with conductive epoxy to the array transducers themselves.

There are three major problems related to the use of passive cables with matrix arrays:

Although cable technology has improved dramatically in recent years, cables with thousands of coaxes are not available. Cost, weight and flexibility are issues.

Interconnecting coaxial cables to the array transducers becomes increasingly difficult.

With higher ultra sound frequencies and more complex matrix arrays, transducer size decreases. The capacitance of the transducer decreases linearly with the area of the transducer. Using a conventional cable results in a critical and fundamental problem—signal loss.

All linear arrays currently on the market use piezoelectric materials as the transducing mechanism from electrical signals to ultrasound (transmitter) and ultrasound back to electrical signals (receiver). The signals are generally in the form of short pulses or tone bursts.

Referring to FIG. 3, there is illustrated a graph of one way signal loss characteristics using a typical coaxial cable as a function of frequency when connected to single elements of types of arrays. The cable used for these calculations has a capacitance of 106 pF that is typical of a two meter long cable used in ultrasound systems. Signal loss occurs because of the mismatch in impedance between the array element and the cable. This signal loss applies to both the transmitting and receiving directions.

In a beam steered array, the transducer dimensions must be about a wavelength in the steering dimension. For example, in a 3.5 MHz (1×128) array the transducer width is about 0.2 mm for a total array length of approximately 64 mm. In the other dimension, the transducer dimensions are a tradeoff between resolution and depth of focus. For a 3.5 MHz array, this dimension is 12 to 15 mm.

As the frequency of the array increases, transducer size decreases, as does transducer thickness, however, the aspect ratio remains constant. Other methods of fabrication such as laser milling or scribing, etching or deposition are under development. At present, they are not well accepted.

Four curves [82], [84], [86] and [88] represent the signal loss associated with probes with no active electronics. (The additional curves, [92], [94], and [96], relate to the invention, and will be discussed in later sections.) In each case, the piezocomposite array elements have the following properties:

Relative dielectric constant, $\in=700$

Width dimension, w=one wavelength at the frequency

Thickness, t=¼ wavelength at the frequency.

Length dimension, L: Varies with type of array, noted below.

The element capacitance in Farads is given by Equation 1.

$$C=8.85\times10^{-12}*\in*w*L/t \quad \text{Eq.1}$$

Curve [82] is calculated for a typical 1 D array with element dimension L=32 wavelengths at the frequency. The signal loss varies from about 50% at 2.5 MHz to 85% at 15.0 MHz.

Curve [84] is calculated for a 1.25 D or 1.5 D array with element dimensions L=5.4 wavelengths at the frequency. The expected signal loss varies from about 82% at 2.5 MHz to 97% at 15.0 MHz. This loss may be intolerable, especially at the higher frequencies.

Curve [86] is calculated for a 1.75 D array with element dimensions L=2.5 wavelengths at the frequency. The expected signal loss varies from 91% at 2.5 MHz to 99% at 15.0 MHz. Curve [88] is calculated for a 2D array with element dimensions L=1.0 wavelengths at the frequency. The expected signal loss varies from 96% at 2.5 MHz to 99.5% at 15.0 MHz. These levels of signal loss in the cable are probably intolerable.

In the transmitting direction, the signal loss can be compensated by increasing the transmitter voltage. On reception, however, the loss in signal results in a decrease in signal to noise ratio. The resulting decrease in signal to noise ratio requires the use of lower frequencies or sacrificing the imaging depth into the body. It is possible to minimize this signal loss without using active electronics in the probe by inserting combinations of inductors and capacitors to impedance match the transducer element to the coaxial line impedance. This is burdensome when there are a hundred elements. With thousands of elements, this presents significant manufacturing problems as well as consuming space within the probe itself.

Referring back to FIG. 1 and to FIG. 4, there is shown in FIG. 4 a beamwidth illustration and comparison as between a linear array and a 1.5 D array. In the probe behind the flex circuit is an acoustical backing [23] that provides mechanical support and acoustical attenuation. When a piezoelectric transducer array [8] is electrically pulsed, two acoustical pulses are generated that travel in opposite directions. Pulse [27] traveling out of the scanhead into the target medium is desired, while the oppositely directed pulse propagating into the backing is unwanted and is absorbed by the backing.

One or more "matching" layers [26] are next in the path of pulse [27]. They serve to improve the coupling of energy from transducer array [8] into the body by matching the higher acoustical impedance array to the lower acoustical impedance of the target medium or body. This matching layer functions in the same way as the anti-reflection coating on an optical lens. The system electronics "focus" the pulse in the scanning plane (or x–z plane) dimension.

Acoustic lens [6] is a simple convex lens as described in Erikson's "Focused Contact Transducer, U.S. Pat. No. 3,387,604, issued 1965 that forms the front surface that contacts the patient's skin. It provides a fixed focus [33] to the sound pulse in the "out-of plane" dimension, which is perpendicular to the scanning plane. Modern systems impose increasingly stringent requirements on arrays. As the number of transducers increases and their size decreases, however, the existing approaches may no longer be feasible or practical. Processing time, touch labor, yield, reliability and cost become limiting issues and new processes are required.

The first matrix array with an integrated circuit was developed by Erikon and Zuleeg in the early 1970's. An 8×8 element, 3.5 MHz receiver array with a preamplifier integrated circuit bump-bonded directly behind each 1 mm×1 mm, Lithium Niobate, single crystal piezoelectric transducer was constructed. Individual transducers could be connected along a row to one of the eight output lines. Although the state of microelectronics was primitive by current standards, the array was shown to have acceptable sensitivity and demonstrated the feasibility of the approach. At that time, the diagnostic ultrasound industry was in its infancy and there was no need for such an array.

In 1995, Thomson Microsonics (TMX), now Thales Microsonics, Sophia-Antipolis, France, described a 1.25 D array, although the paper was entitled a 1.5 D array. This array did not have active circuitry in the scanhead. Individual transducers were connected through a separate coax cable.

More recently, TMX proposed a 128×7 transducer curved linear array. Despite the title, this was also a 1.25 D array, by the definition adopted here. Active switching electronics in the scanhead were described, but no additional electronics were mentioned. A flex circuit was used for the interconnections between the array transducers and the electronics. There was no integrated circuit directly connected to the array. Signals are multiplexed through 128 coax lines.

In the U.S. government funded BUDI (Battlefield Ultrasonic Diagnostic Imager) program, a real-time, three dimensional ultrasound camera, intended for Army medics in combat situations, was designed and feasibility was proven. In this camera, an acoustical lens was used to image a volume onto a 128×128 (16,384 element) 5 MHz matrix array, as was disclosed in Erikson et al's, "Imaging with a 2D Transducer Hybrid Array", in *Acoustical Imaging*, Vol. 24, Ed. H. Lee, Plenum Publishing Corp., New York, 2000. Each transducer of the piezocomposite array had a custom integrated circuit bump-bonded directly behind it using micro-solder balls. The piezocomposite array was air-backed, in other words there was a small air space between the array and the IC. The bump bonds were the only mechanical and electrical connections between the array and the IC. No matching layer was used on the front side of the array.

Each unit cell of the ROIC (read only integrated circuit) contained a preamplifier, signal processing, a limited amount of sampled data storage and multiplexing. The silicon was two side-buttable, permitting tiling of four, 64×64 pieces into a square 128×128 array.

The water tank images that were made demonstrated the viability of the acoustical lens and the performance of the receiver array. Most importantly, the concept of bump-bonding a matrix array directly to an integrated circuit was revalidated. Important parts of this technology are now protected by U.S. and foreign patents including Butler, N., et al, "Two Dimensional Transducer Integrated Circuit", U.S. Pat. No. 5,483,963, issued Jan. 16, 1996; White, T., et al, "Ultrasonic Array with Attenuating Electrical Interconnects", U.S. Pat. No. 5,732,706, issued March 1998; and Erikson, K. R., et al, "Ultrasonic Camera", U.S. Pat. No. 6,159,149, issued December 2000. This system has long term potential for diagnostic ultrasound applications; however, it is not useful for current medical ultrasound systems.

In summary, recent advances in transducer technology and integrated circuit fabrication have clearly extended the potential for improvements and extensions in the manner in which ultrasound applications are implemented.

BRIEF SUMMARY OF THE INVENTION

One embodiment of the present invention provides an orthogonally switchable matrix array transducer system for ultrasound imaging. The system includes a multiplicity of subarrays of N by N transducers, and a bus including N vertical bus lines and N horizontal bus lines. N is at least 2. Each of the transducers of at least one subarray is switchably connected to a vertical bus line and to a horizontal bus line, thereby enabling reconfiguration of the at least one subarray between a horizontal mode of operation and a vertical mode of operation. A summer circuit may also be included which is adapted for integrating signals output by one or more of the subarrays into a common output signal that can be processed by a control system.

Another embodiment of the present invention provides a method for performing ultrasound imaging with a matrix array transducer probe. The transducer probe includes a multiplicity of tiled subarrays of transducers. The subarrays are oriented in a pattern having a vertical component overlapping a horizontal component, and at least one of the subarrays is switchable between a horizontal operating mode and a vertical operating mode. Output signals of the tiled subarrays can be integrated into an output signal. The method includes recording one or more ultrasound images in the horizontal operating mode, switching between the horizontal operating mode and the vertical operating mode, and recording one or more ultrasound images in the vertical operating mode. Note that the recording steps can be performed in any order. The method may further include integrating the ultrasound images recorded in the horizontal operating mode with the ultrasound images recorded in the vertical operating mode so as to generate real-time, three dimensional ultrasound imagery. In addition, the switching between the modes may be performed in real-time.

Another embodiment of the present invention provides an orthogonally switchable matrix array transducer system. The system includes a multiplicity of subarrays of transducers configured as orthogonally oriented arrays that include an area of overlap. The system further has a bus that includes vertical bus lines and horizontal bus lines, where each of the transducers of at least one subarray is switchably connected to a vertical bus line and to a horizontal bus line, thereby enabling real-time reconfiguration of the at least one subarray between a horizontal mode of operation and a vertical mode of operation. A summer circuit may also be included which is adapted for integrating signals output by one or more of the subarrays into a common output signal.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE FIGURES

FIGS. 2A–2E are a series of diagrams explaining the significance of the dimensional nomenclature by which the acoustical arrays are characterized in this disclosure.

FIG. 3 is a chart expressing one way signal loss in coax cable with and without impedance matching electronics in the probe head.

FIG. 6 is a simplified diagram view of the interface electronics at the system console end of the probe cable of the preferred embodiment of FIG. 5A.

FIG. 18A is a cross section view diagram of the sector scanning pattern of a transducer array into a target medium.

FIG. 18B is a partial close up view of the diagram of FIG. 18A, illustrating respective path lengths and differences from one edge of the full array of a subarray to the other.

DETAILED DESCRIPTION OF THE INVENTION

The invention combines two orthogonal 1.5 D or 1.75 D arrays, either of which may be electronically selected. The arrays have common signal processing and beamforming contained in integrated circuits directly connected to each transducer of the array.

Figure 1:
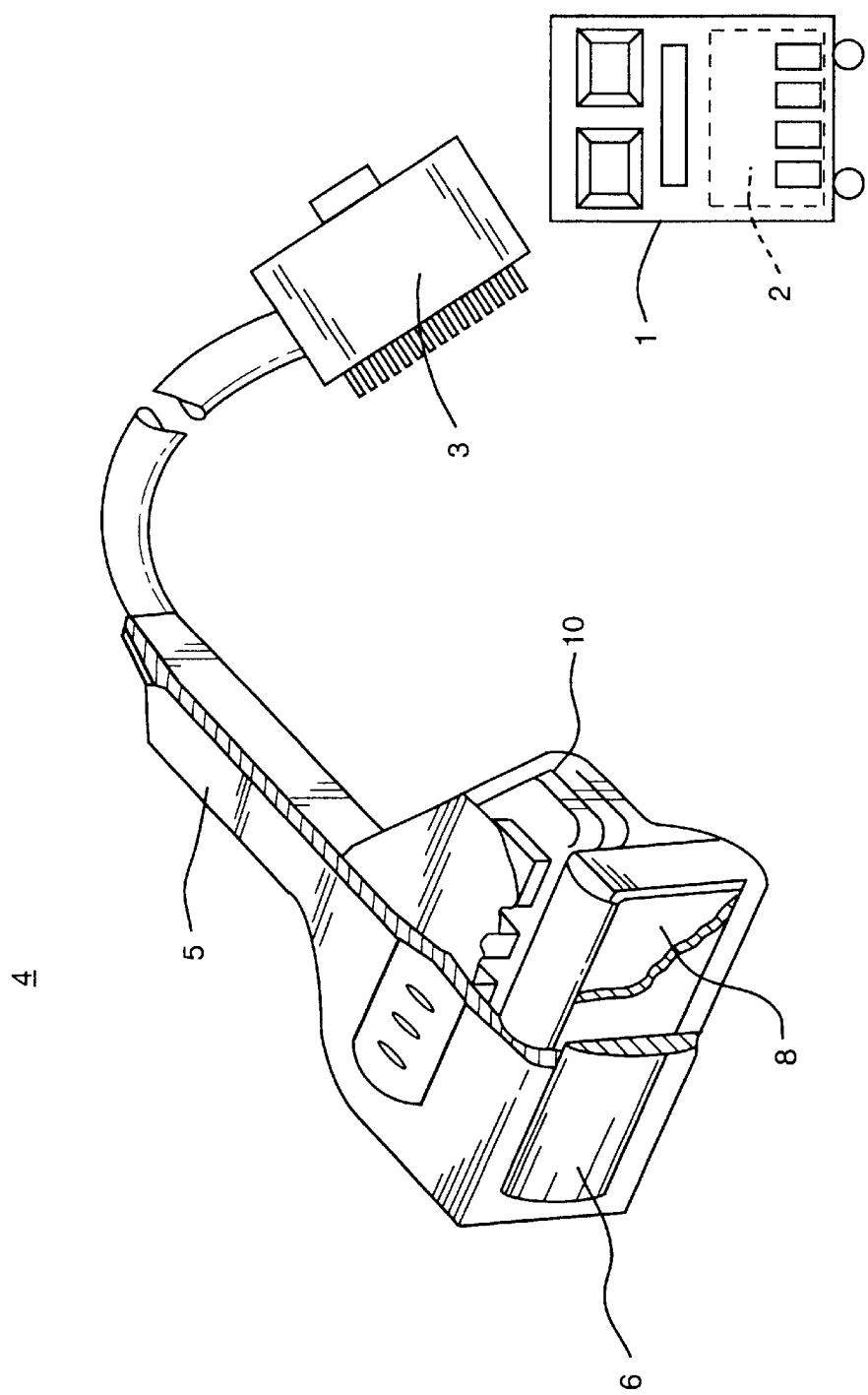
FIG. 1 is a diagrammatic view of a conventional linear array ultrasound imaging system, with the probe assembly shown in a partial cut away view.
Figure 4:
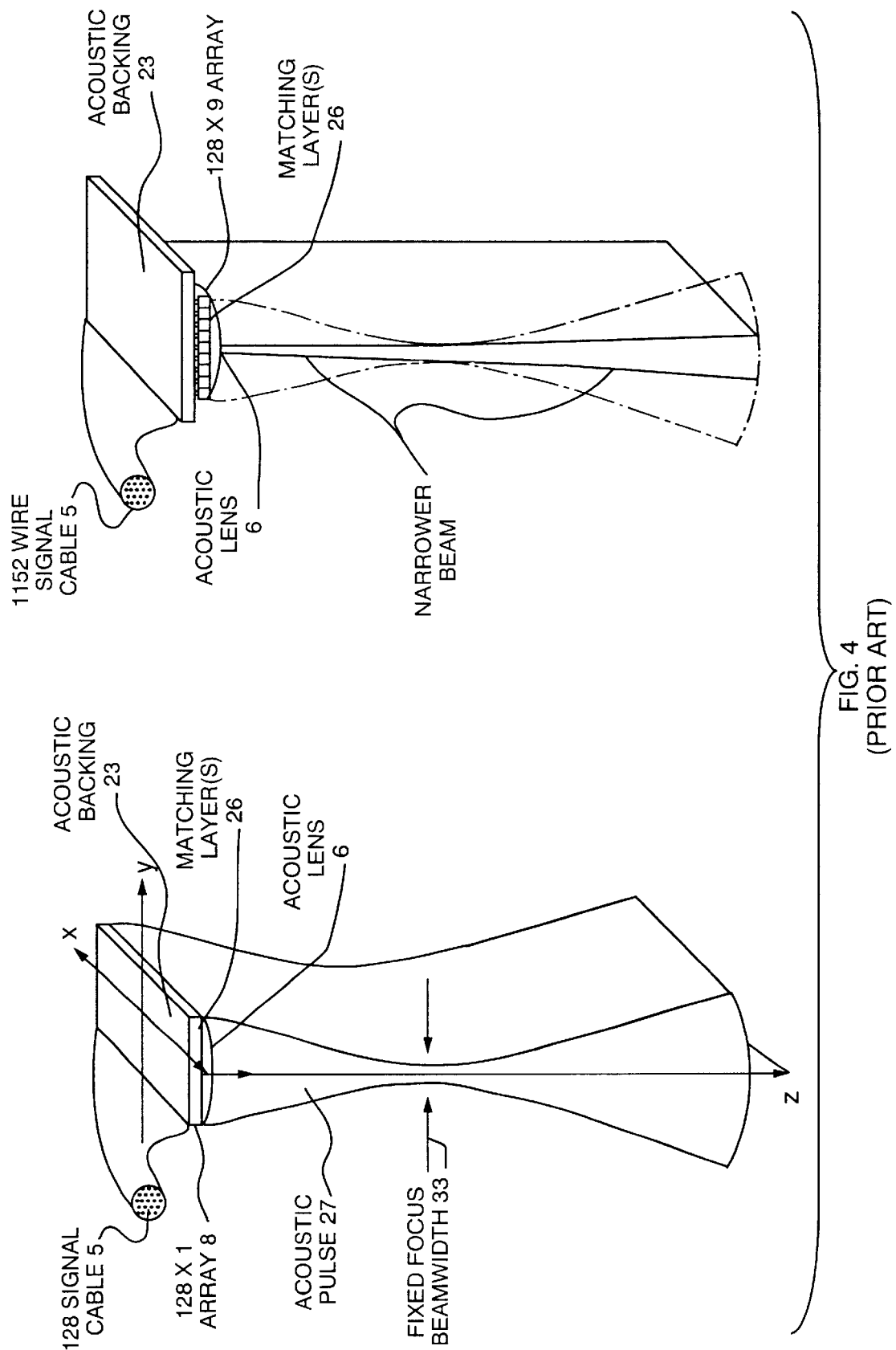
FIG. 4 is a diagrammatic beamwidth comparison of a conventional linear array versus a 1.5 D array.
Figure 5A:
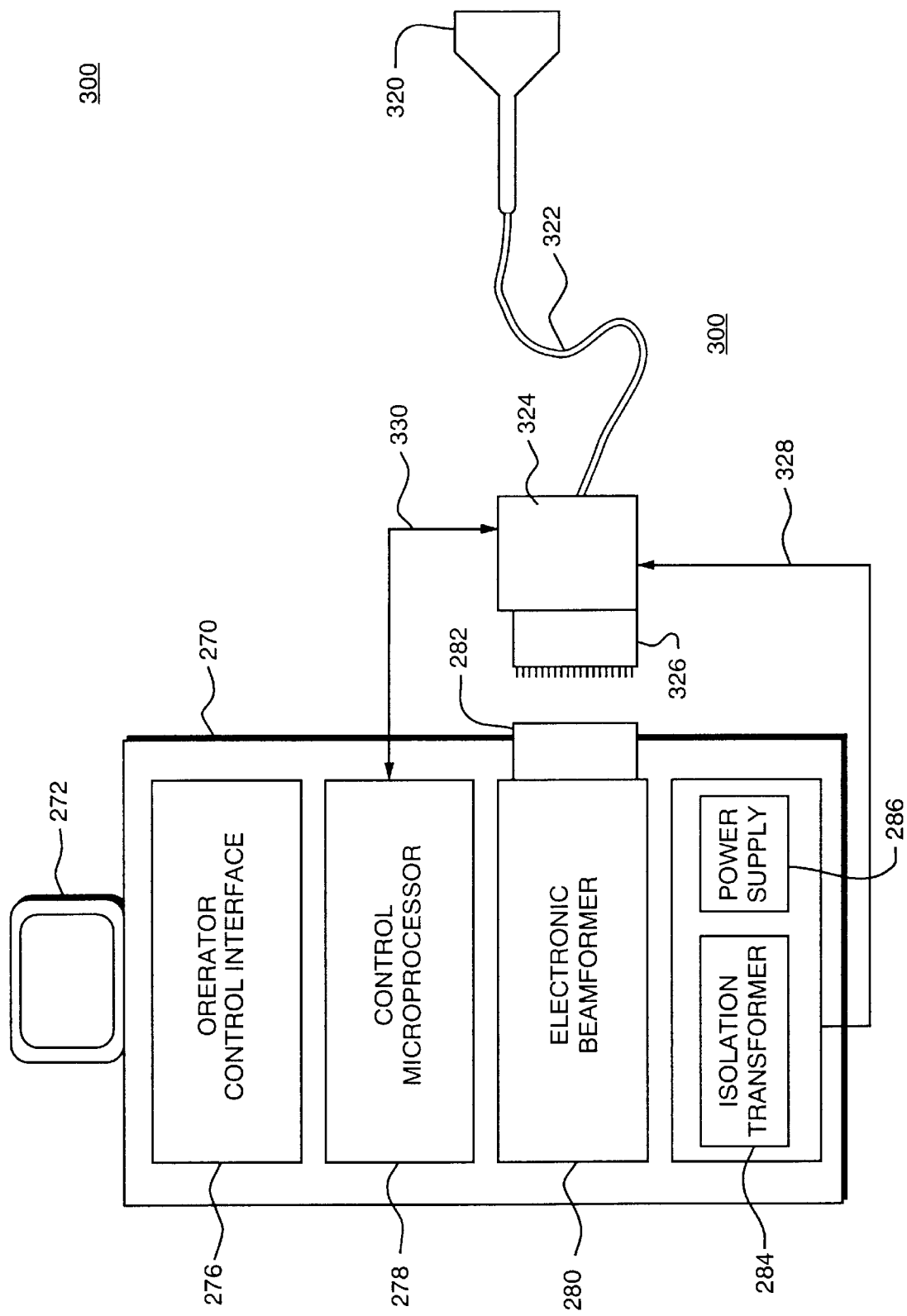
FIG. 5A is a diagrammatic illustration of a preferred embodiment, orthogonally reconfigurable, probe assembly connected by a coax cable to an ultrasound system console.
Figure 5B:
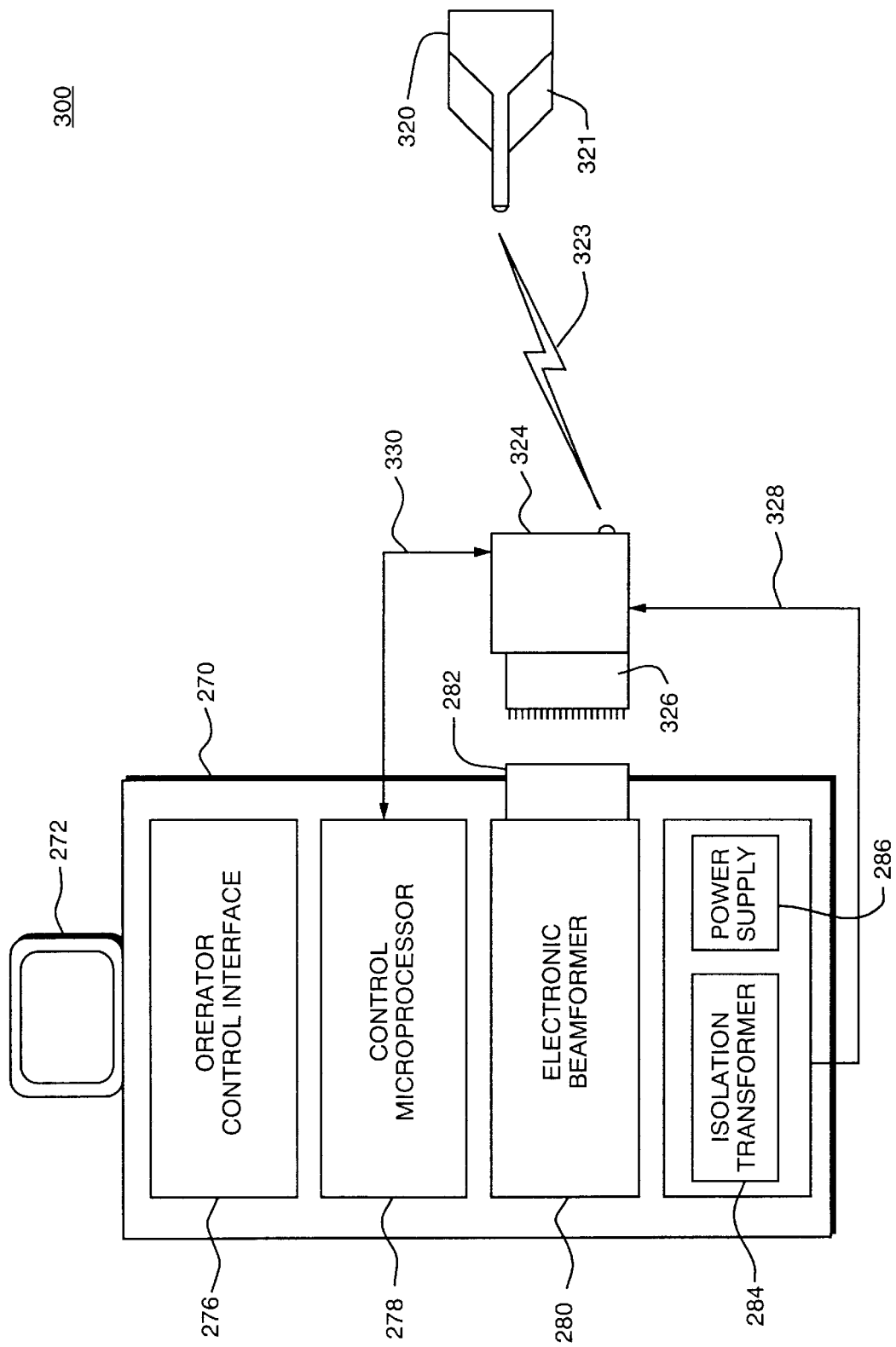
FIG. 5B is a diagrammatic illustration of the preferred embodiment of FIG. 5A, but with the probe assembly connected by a wireless data communications system to the ultrasound system console.

FIGS. 5A and 5B illustrate a preferred embodiment orthogonally reconfigurable probe system [300] attached to a typical ultrasound system [270]. The ultrasound system is comprised of a display [272], an operator control interface [276], a control microprocessor [278], an electronic beamformer [280], an isolation transformer [284] and a power supply [286]. These elements are well known to those knowledgeable in the ultrasound imaging art.

In FIG. 5A, the orthogonally reconfigurable probe system [300] consists of probe [320], interconnecting cable [322] and probe interface [324]. Probe interface [324] has a multi-pin connector [326] which plugs into beamformer [280] via mating connector [282]. Connector [282] may be the same connector used for a conventional probe.

In FIG. 5B, probe [320] includes a battery pack [321] as an independent power source, and communicates data to and from probe interface [324] via a wireless data communications link [323]. There may be a connection to a local power source in lieu of or in addition to an on-board battery. In other respects, FIGS. 5A and 5B are the same.

Probe interface [324] derives electrical power from ultrasound system [270] from either isolation transformer [284] or power supply [286]. This is a requirement for electrical safety. Additionally, probe interface [324] derives control signals from ultrasound system [270] via signal line [330]. This signal line may use a standard bi-directional signaling protocol such as RS-232 or other serial or parallel communication protocols.

The problem of signal loss due to impedance mismatch between the transducer and the coaxial cable was discussed in the background section. A solution is to use active electronics near the transducer. A preferred method is to use an integrated circuit directly behind each transducer for impedance matching. The stray capacitance in such an integrated circuit is typically less than one picofarad (pF) which is less than 1% of the typical value in a coaxial cable. This results in significantly less signal loss.

Referring again to the figures, as is further explained below, there are one or more integrated circuits in probe [320] between the array transducers and interconnecting cable [322] to match the impedances of the transducers to the signal conductors in the cable. Dramatic improvements in signal level through the coaxial signal conductors are achieved, as compared to the prior art practice. Referring back to FIG. 3, and using the same calculations previously described, curves [90], [92] and [94] represent the signal loss in similar arrays when used with active electronics located adjacent each transducer of the array.

Curve [90], using an integrated circuit with 750 fF stray capacitance with same 1.25 or 1.5 D array as curve [84], shows a 3% signal loss at 2.5 MHz and only 20% loss at 15 MHz. Curve [92] is a similar curve for the 1.75 D array and should be compared to curve [86]. Losses vary from 7% to 35% over the frequency range.

The smallest element, a 2D array as shown in curve [94], has a loss ranging from 15% at 2.5 MHz to 57% at 15 MHz. When compared to the 1 D array in common use today, this is a substantial improvement over the passive cable calculations represented by curves [82]–[88] as discussed previously.

Referring now to FIG. 6 in conjunction with FIG. 5, there is shown the functional block diagram of the internal electrical circuits of probe interface [324]. Multi-pin connector [326] typically has 128 or more pins [325] to connect channel signal wires from beamformer [280] to probe interface [324]. Only channels 1 and 128 are shown for clarity.

Signal wire [327] is further connected to one of 128 T/R switches and to one of 128 amplifiers in electronics module [360], which is discussed in more detail below. Microcontroller [332] receives control information from ultrasound system control microprocessor [278] via control line [330]. This information would typically include vertical or horizontal probe orientation, transmitter focus range, receiver focus range, and any other necessary or useful control information. Information to setup the scanning parameters for the each entire frame would typically be transmitted in advance of the transmitter pulse or frame data acquisition.

Figure 9:
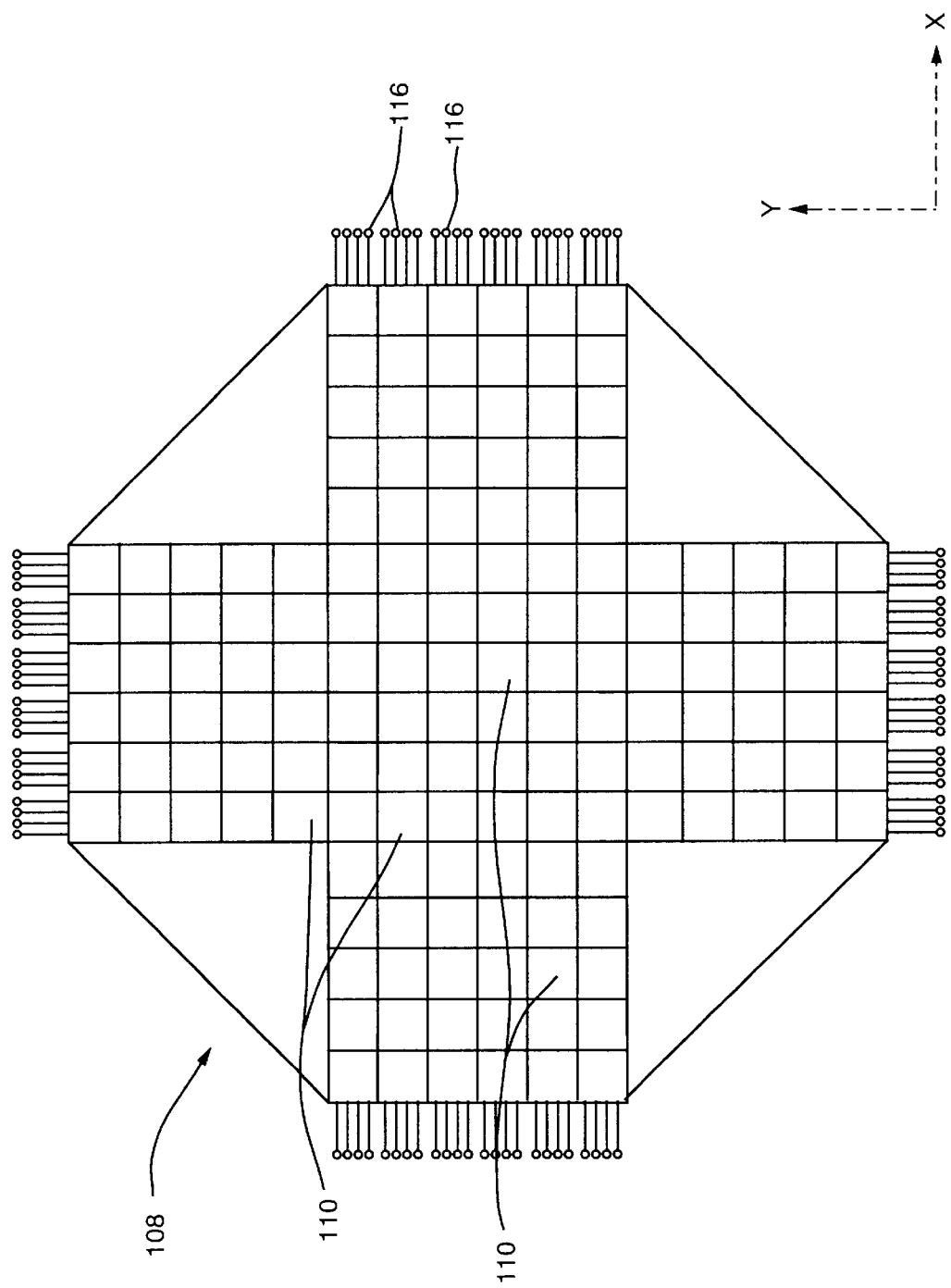
FIG. 9 is a top-view diagram of an orthogonally reconfigurable, integrated matrix, acoustical transducer array configured in a cross pattern of 128, 8×8 transducer tiles.
Figure 10:
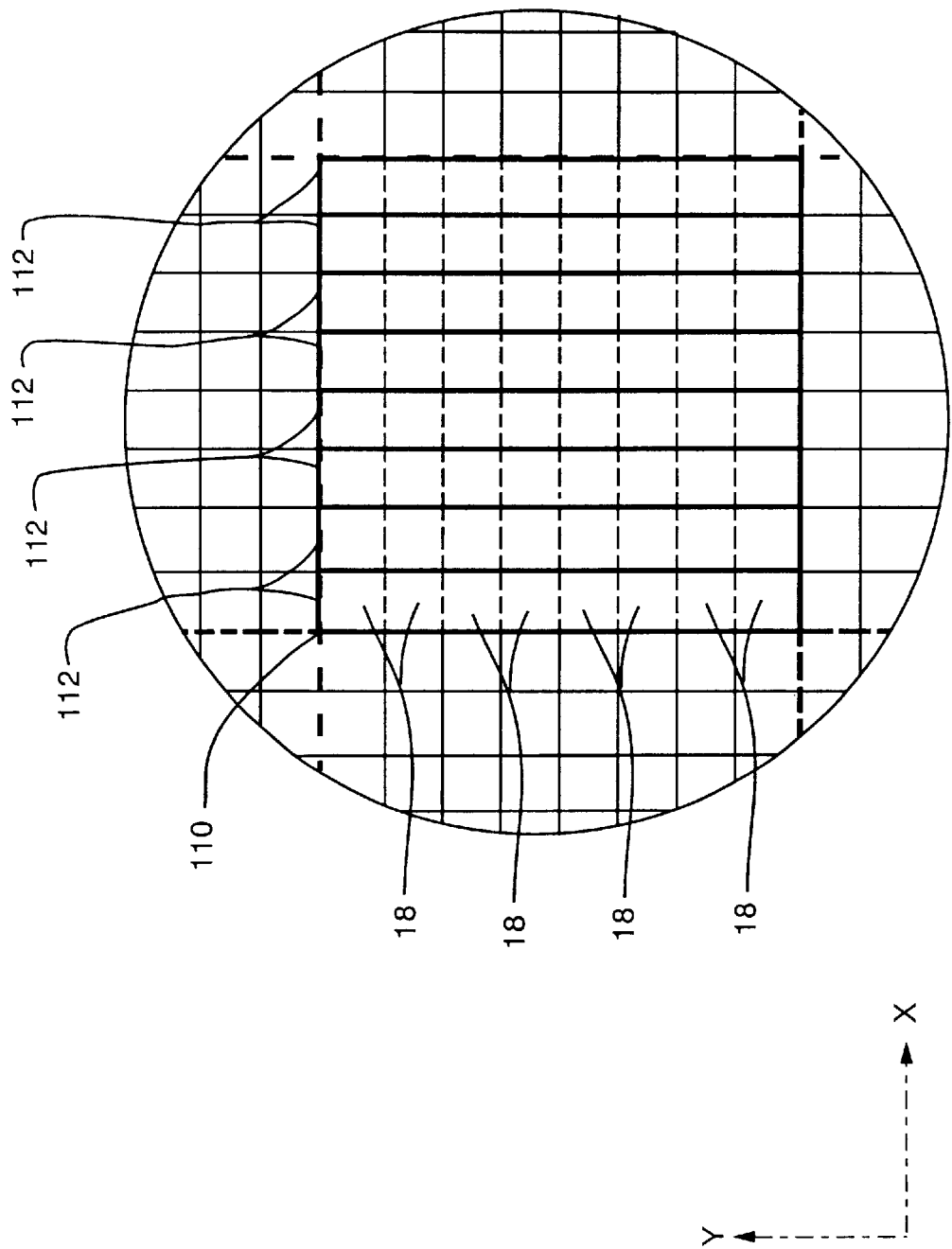
FIG. 10 is a partial close up view of the diagram of FIG. 9, illustrating the vertical strip array configuration of an 8×8 tile.
Figure 11:
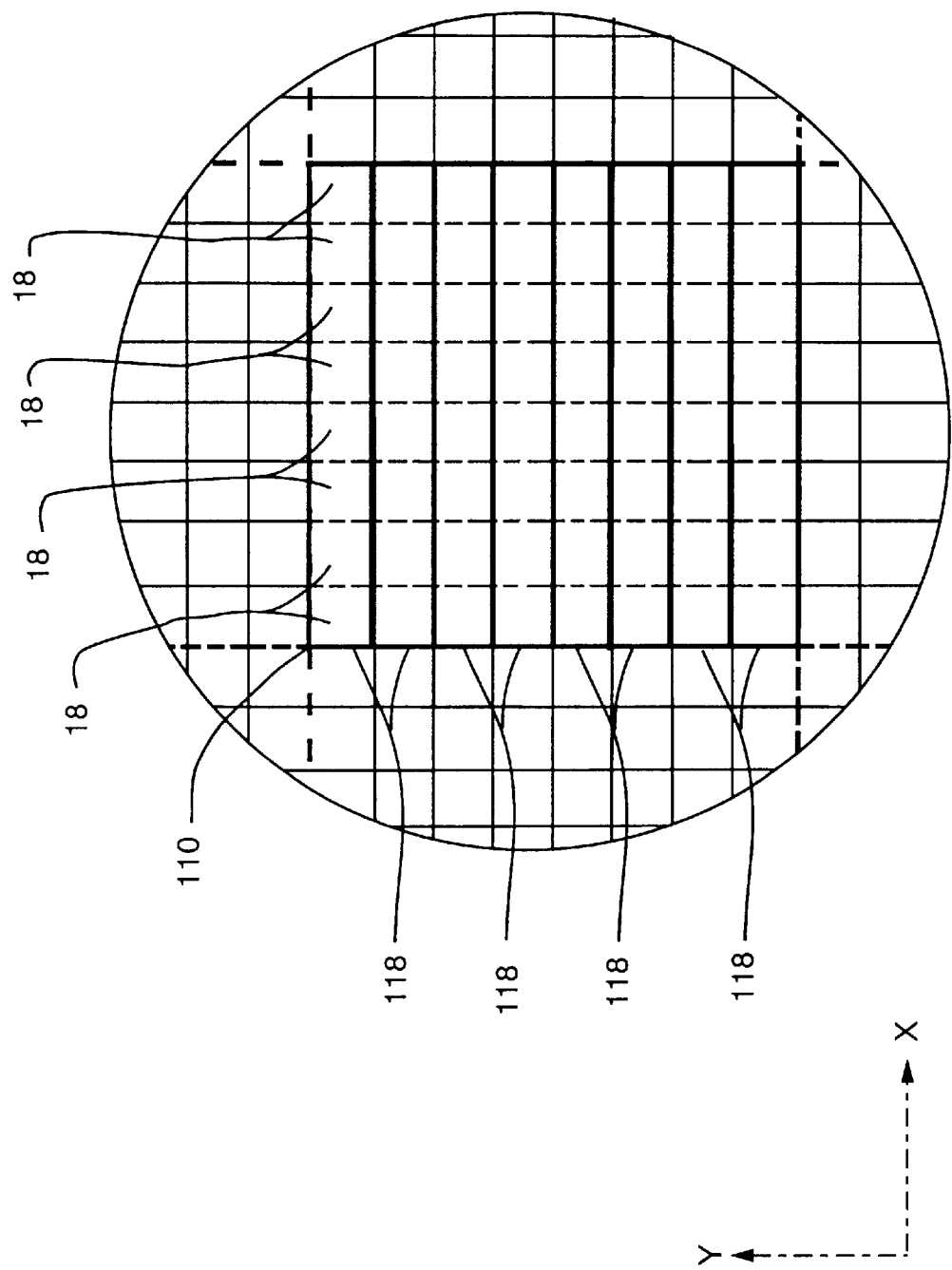
FIG. 11 is a partial close up view of the diagram of FIG. 9, illustrating the horizontal strip array configuration of an 8×8 tile.

The primary function of microcontroller [332] is to translate the scanning parameters into time delays for each of the transducer array strips, either vertical [112], FIG. 10, or horizontal [118], FIG. 11, contained in probes tiles [110], FIG. 9. This information is passed on to probe [320] via signal line [350]. Microcontroller [332] may also send status information such as probe type, correct probe operation, and related information, back to processor [278] via line [330].

Power supply [342] derives it power from ultrasound system [270] via wire(s) [328]. It may derive other voltages as required to power the electronics in interface [324] or in probe [320]. Bi-directional control line [350] is used to send information to, and receive status information from probe [320]. Wire [116] sends transmitter pulses to, and received signals from probe [320]. Cable [322] is a bundle of wires, typically 128+32=156 total wires. These wires are usually coaxial cables to minimize crosstalk between wires.

Figure 7:
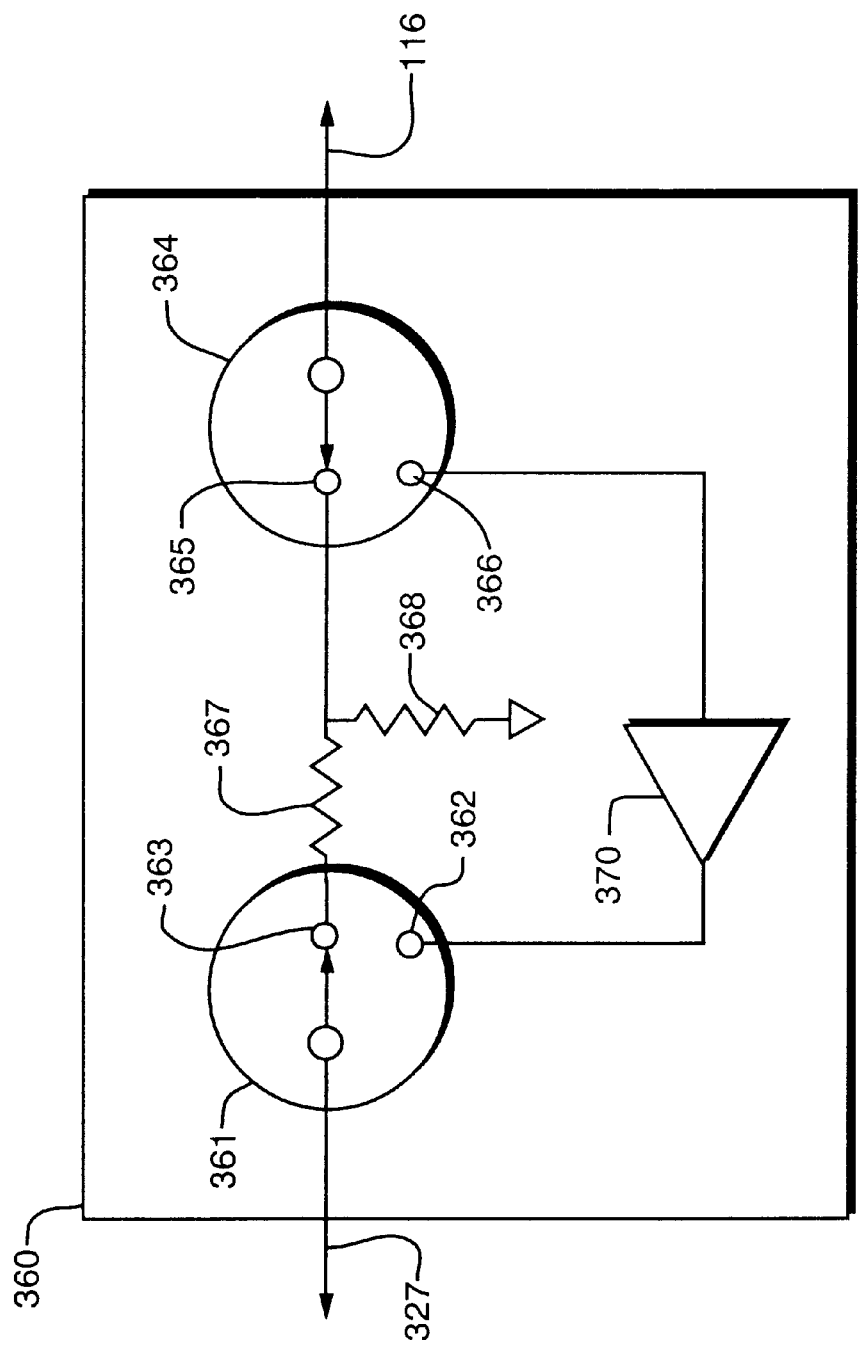
FIG. 7 is a functional block diagram of a transmit/receive switch and amplifier module in the interface electronics of FIG. 6.

Referring to FIG. 7, electronics module [360] includes switches [361] and [364] and amplifier [370]. The function of the two switches is to isolate amplifier [370] from any high voltages coming from ultrasound system [270] that might damage the amplifier. Such high voltage pulses are typically used to generate ultrasound pulses in passive probes.

In FIG. 7, if switch [361] is in position as shown, in the transmission mode conducting to node [363], the transmitted pulse from the system will pass to resistors [367] and [368]. The values of these resistors are chosen to attenuate the transmitted signals from ultrasound system [270] of FIG. 5, to voltages that are safe for the rest of the probe electronics. This signal then serves as a synchronization pulse for the probe channel. Switch [364], when conducting with node [365] as shown, passes the transmitter synchronization pulse to probe [320] as in FIG. 5, via respective wires [116]. When the system is in the receiving mode, switches [361] and [364] are switched to nodes [362] and [366], respectively. This allows returning signals to be routed through amplifier

[370], back through conductor [327], and pin [325] into beamformer [280].

Figure 8:
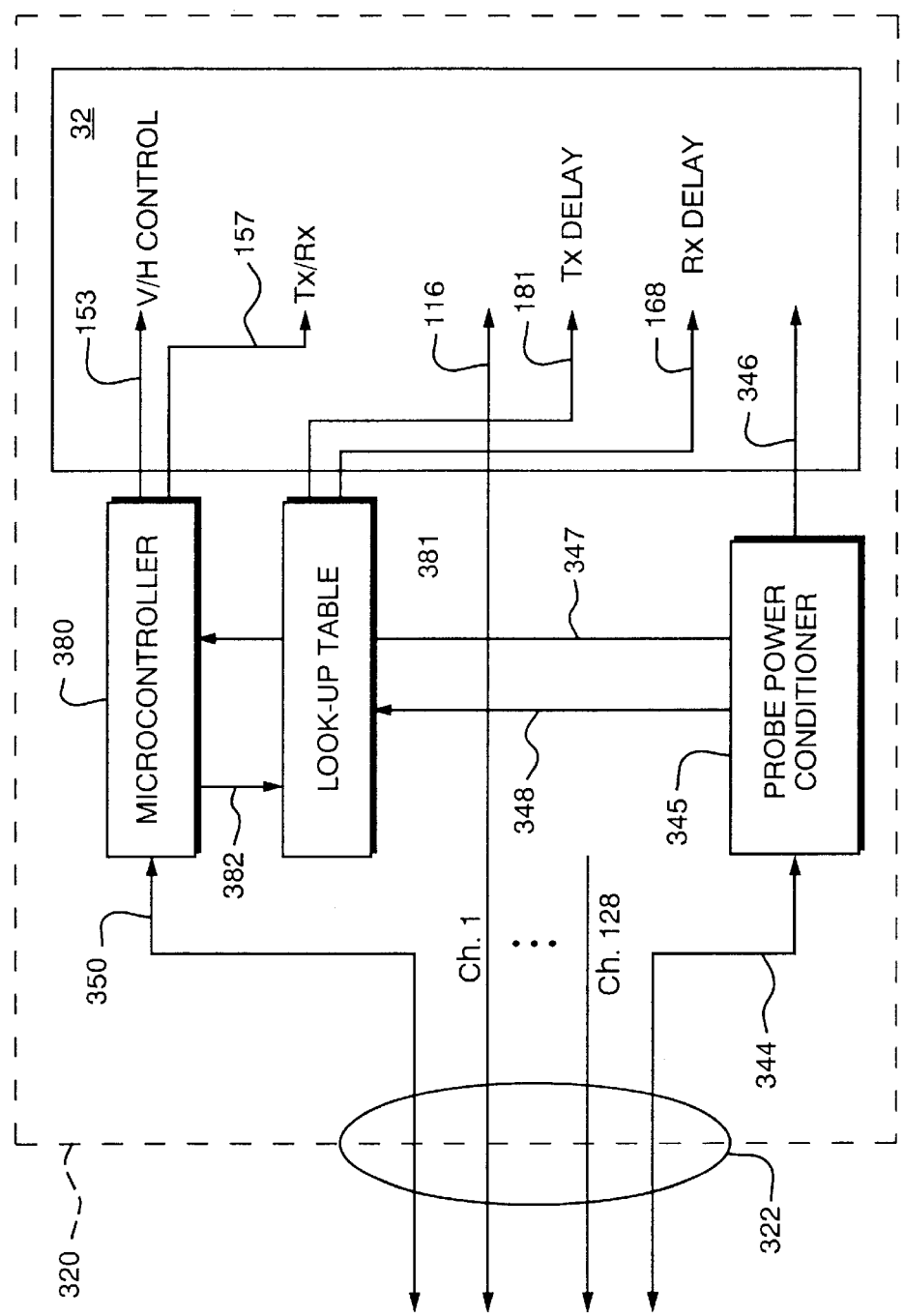
FIG. 8 is a functional block diagram of the electronics in the probe supporting the integrated circuit transducer array of the preferred embodiment of FIG. 5A.

Referring to FIG. 8, there is illustrated the functional block diagram of the supporting electronics inside probe [320]. Time delays for each strip array of transducers and each tile of strip arrays, as explained below and illustrated in FIGS. 9, 10, and 11, plus any other signals, come into to microcontroller [380] via bi-directional path [350]. Microcontroller [380] interprets the time-delay data and places it into look-up table [381] via signal line [382]. This look-up table permits rapid, easy access.

Transmitter delays may be sent to respective integrated circuits [32], there being one closely connected or integrated into each tile array of transducers and to the individual transducers of the tile, over signal line [181]. Similarly, receiver delays may be sent over signal line [168]. These delays, which must change in real-time as the pulse propagates into the subject under test, are typically loaded into a memory buffer in integrated circuit [32].

As has been discussed earlier, flip chip mounting and electrode bump bonding techniques and related advances in chip fabrication, already in commercial use and still evolving, permit the close connection or integration of transducers and transducer arrays of various types with directly supporting power, control logic and data circuitry such that individual transducers and desirable groups of transducers can be "pre-wired" at the chip level, thereby shifting a significant portion of the system circuitry closer to the transducer array than was possible only a short time ago.

Vertical or horizontal selection inputs may be sent to IC [32] via control line [153] from the control console and interface box. Transmitting or receiving is selected in IC [32] by means of control line [157]. Electrical power for these probe electronics is delivered by wire(s) [344] to probe power conditioner [345] which may consists of voltage regulators or the like. This conditioned power is sent to microcontroller [380] via wire [347], to look-up table [381] via wire [347] and to IC [32]via wire [346].

FIG. 9 is a top-view diagram of one aspect and embodiment of the invention, depicting an orthogonally reconfigurable, integrated matrix, acoustical transducer array [108] consisting of a cross pattern of 128 subarrays, each of which is an 8×8 transducer tile [110]. This embodiment requires only 156 coaxial wires connecting the probe to the ultrasound console. In close up view FIG. 10 of array [108] of FIG. 9, the 64 individual transducers in any tile [110] are electrically connectible by means of the electronics of an integrated circuit [32] of FIG. 8 into 8 vertical strips [112] consisting of 8 transducers [18] per strip. In this configuration, sector scanning in plane XZ is enabled. As shown in close up FIG. 11, these same 64 transducers of tile [110] are reconfigurable for connecting into 8 horizontal strips [118] of 8 transducers [18] for sector scanning in the YZ plane.

The enabling technology for this invention is the integrated array. By including signal processing immediately behind the array tile in the form of integrated circuit [32], only one signal input/output wire is required per 8×8 tile. Thus, for the array described in this example, only 156 total wires are required. This number of conductors is within the present commercially available, state-of-the art coaxial cable technology.

Figure 12:
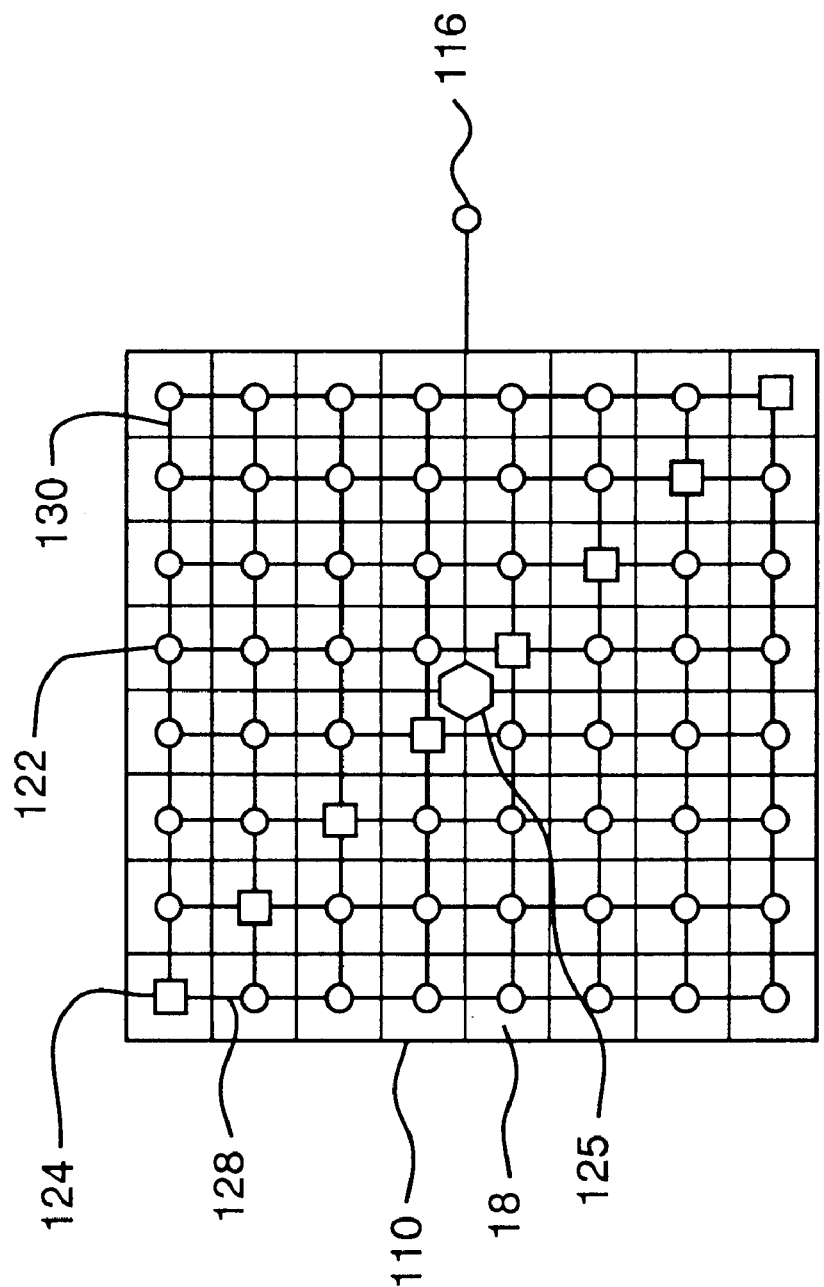
FIG. 12 is an electronic block diagram of the various circuits and interconnections contained in the integrated circuitry behind each tile of the array of FIG. 9.

FIG. 12 is an electronic block diagram of the various functional blocks contained in the integrated circuitry behind each tile [110]. Included are switch nodes [122], switch/transmitter/receiver/signal processing nodes [124] and a transmitter delay/receiver summer block [125]. Tile [110] has eight vertical electrical interconnecting bus lines [128] and 8 horizontal electrical interconnecting bus lines [130].

Figure 13:
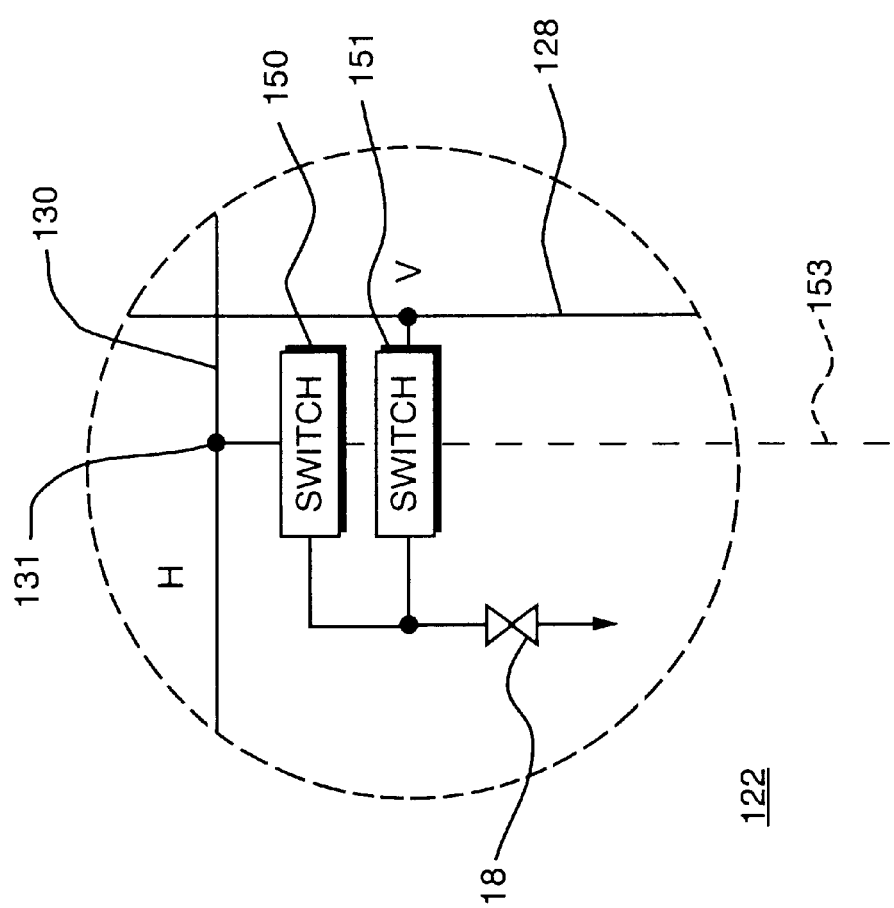
FIG. 13 is a switch node from the subarray IC of FIG. 12, for connecting a transducer to either a vertical or a horizontal strip bus.
Figure 14:
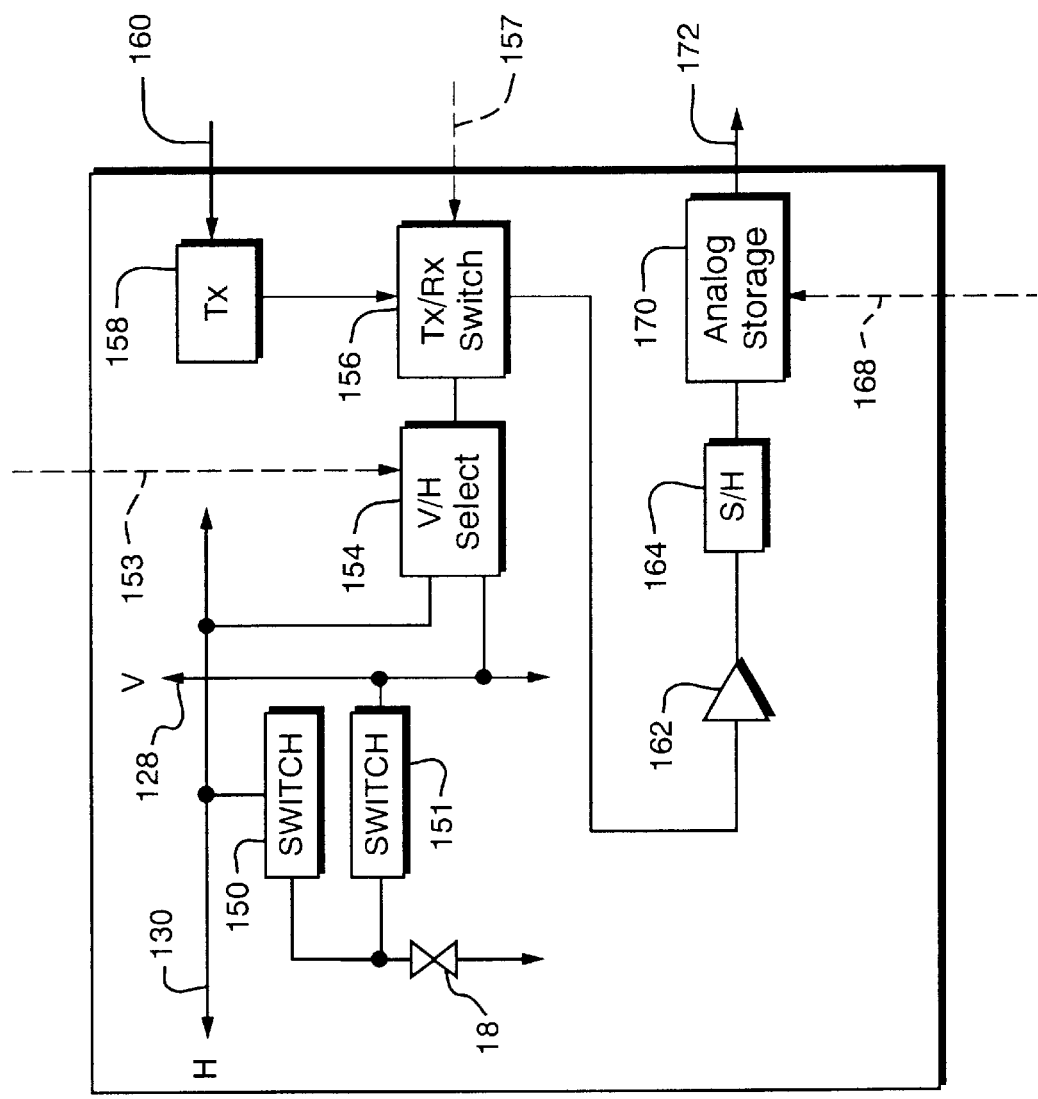
FIG. 14 is a switch/processing node or circuit in the tile circuitry of FIG. 12, similar to the switch of FIG. 13 but including switching for configuring the subarray between vertical and horizontal modes, and between transmitting and receiving modes.

More specifically, every transducer or unit cell in IC [32] has either a switch node [122], the functionally equivalent circuit of which is shown in detail in FIG. 13, or a switch/processing node [124], the equivalent circuit of which is shown in detail in FIG. 14, which are used to connect the transducer to either a vertical [128] or a horizontal bus [130]. The switches are operated by a common control input to connect all transducers in the tile to either the vertical bus lines or the horizontal bus lines. Further, the switch/processing nodes [124] are arranged to connect either of all horizontal or all vertical bus lines, as determined by the vertical/horizontal control input, to a summer node [125], the circuit of which is shown in detail in FIG. 15, and to which signal conductor [116] is attached. Thus, the vertical strips of 8 transducers [112] shown in FIG. 10 or the horizontal stripes of 8 transducers [118] shown in FIG. 11 may be connected through respective tile summers to signal lines 116.

For clarification, solid black lines in FIGS. 12 through 15, such as [130] are to be interpreted as interconnecting wires in IC [32], whereas solid black circles such as [131] represent electrical connections. Where solid black lines cross, they are electrically isolated unless connections [131] are present.

Node [122] is illustrated in FIG. 13. Horizontal switch [150] may be used to connect array transducer [181] to horizontal bus [130]. Similarly, switch [151] may be used to connect array transducer [18] to vertical bus [128]. Switches [150] and [151] are mutually exclusive. They are controlled by V/H selector signal line [153] from other parts of the IC that are themselves controlled by external electronics. Switches [150] and [151] throughout the IC are high voltage, low stray capacitance devices. They must be capable of standing off the transmitter voltage, which may be as high as 50 volts. High voltage DMOS transistors, well known to the semiconductor art may be used. Furthermore, to achieve low stray capacitance, a Silicon-On-Insulator (SOI) process is a preferred method.

FIG. 14 describes node [124] and includes the same switches as FIG. 13 plus additional signal processing electronics, including:

1. Vertical or horizontal bus selector switch [154] controlled by signal line [153] from microcontroller [380];
2. Transmit/receive (Tx/Rx) selector switch [156], which is controlled by signal line [157];
3. Transmitter (Tx) [158], which receives a signal from transmitter time delay electronics [182] (in FIG. 15) via signal line [160];
4. Preamplifier [162];
5. Sample and hold (S/H) processor [164];
6. Receiver time delay (Rx time delay) selection signal line [168];
7. Time delay function and read-out [170] which is typically an analog shift register composed of storage capacitors.

Transmitter [158] may also be composed of high voltage DMOS switches, such that a bipolar impulse signal received on signal [160] from the transmitter delay is translated to a high voltage signal. This high voltage signal is applied to the vertical or horizontal buses through V/H select switch [154]. This signal is then routed to all transducers [18] connected to the bus, where it generates an acoustical pulse signal, which is similar to the signal received on [160]. Switches [154] and [156] are also high voltage DMOS, similar to switches [150] and [151].

During reception of signals, time delay [170] is continually being loaded from sample-and-hold processor [164]. The sampling rate is determined by the ultrasound frequency employed. This frequency is typically 10 times the highest frequency component in the ultrasound transducer frequency spectrum.

Selection line [168] determines the time delay introduced into the sampled signal from the transducer. There is a minimum delay of one sample time. The maximum delay is determined by the number of storage capacitors and the sampling frequency. The selection of the delays will be discussed below.

Figure 15:
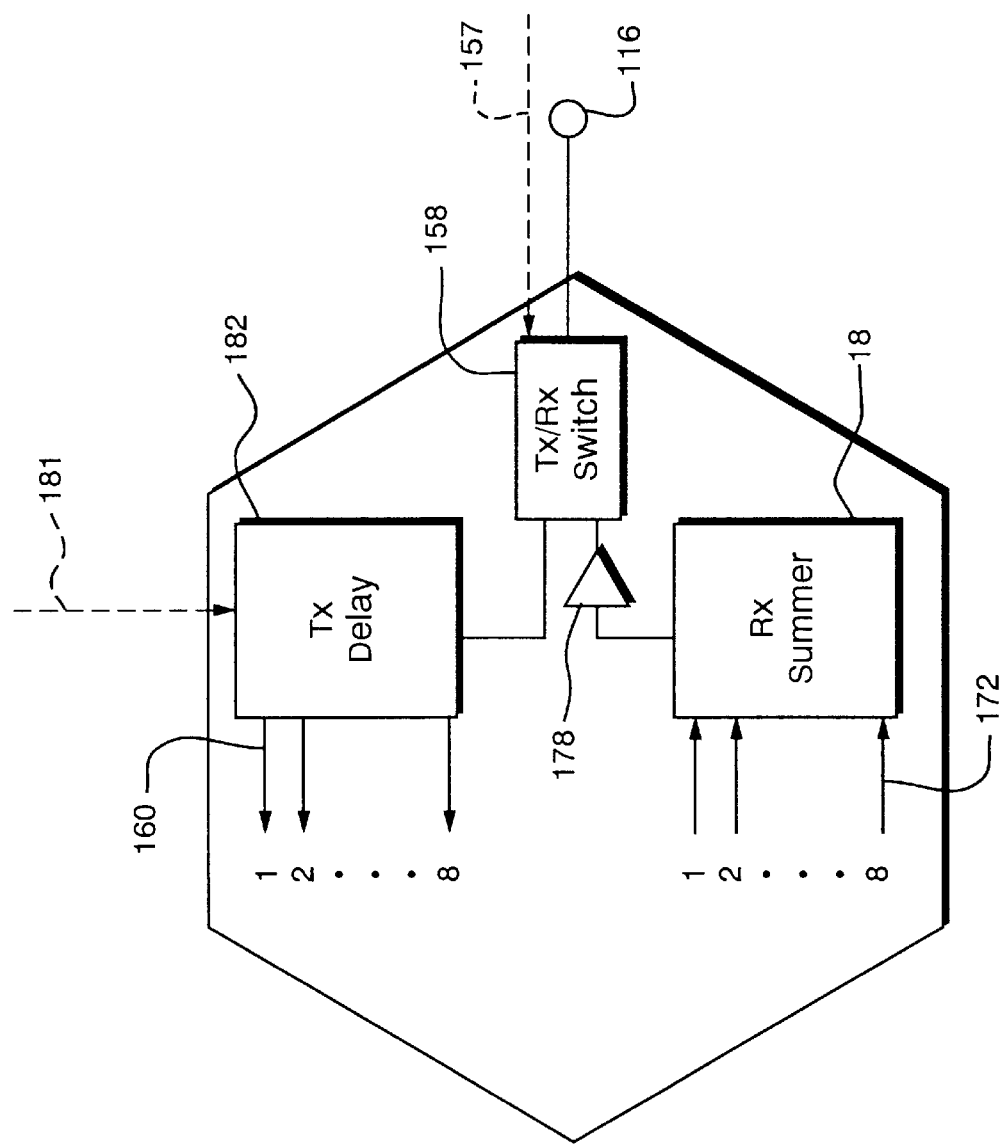
FIG. 15 is a summer circuit of the tile of FIG. 12, which distributes transmit signals and collects and sums received signals from the strip busses.

FIG. 15 depicts the circuitry of node [125] of any tile [110], and includes:

1. Transmit/receive (Tx/Rx) selector switch [158] controlled by selector line [157];
2. Transmitter time delay [182], which outputs signals to the eight transmitters through signal lines [160]. These outputs are time-delayed duplicates of the bipolar transmitter signal input [116]. Time delayed outputs 1 through 8 are generally different and are selected to provide transmitted beam steering in the tile. The amount of time delay is selected by signal line [181];
3. Receiver summer [184] which receives time delayed signals from the eight time delay modules [170] of FIG. 14 through signal lines [172] and outputs the summed signal to driver amplifier [178];
4. Input/output line [116] from amplifier [178] through Tx/Rx switch [158] and back through cable [322].

Figure 16:
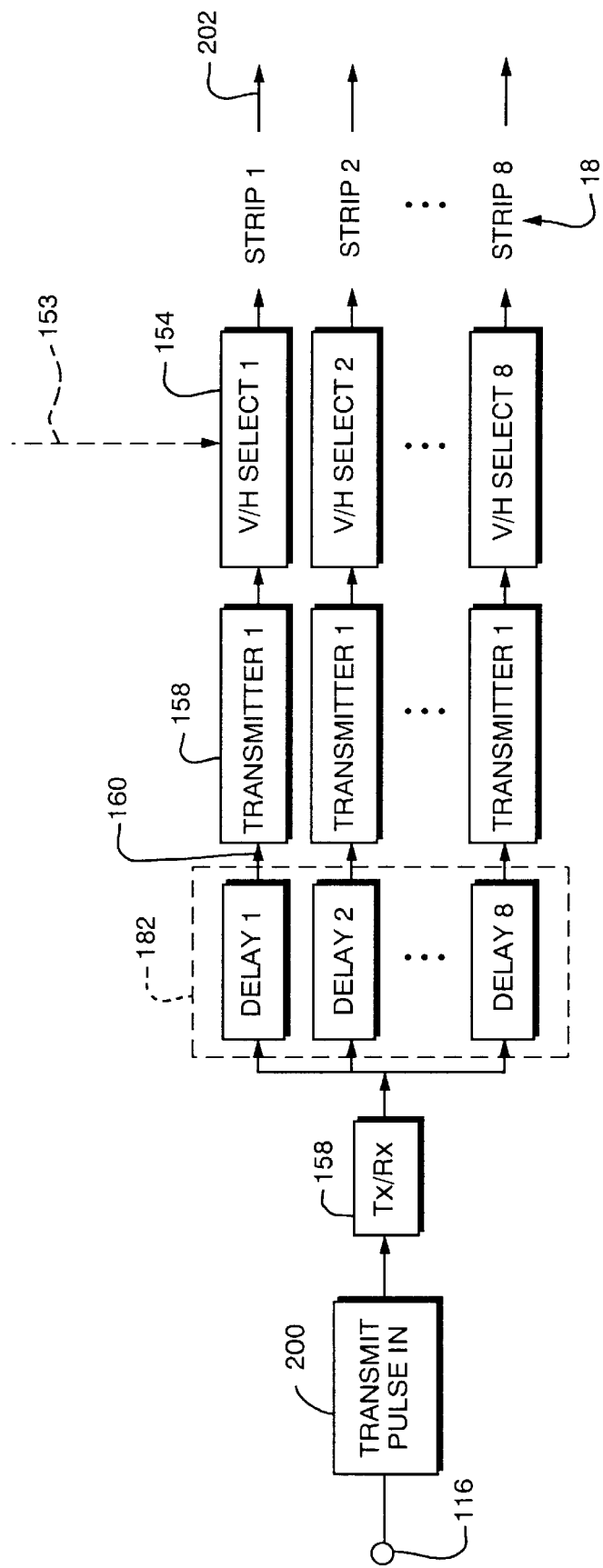
FIG. 16 is a block diagram describing the signal processing flow in a subarray of FIG. 12 in the transmit mode.

FIG. 16 describes the signal processing flow on transmit, the references pertaining to FIGS. 5–15:

All Tx/Rx switches [156], [158] are set to transmit (Tx) by signal line [157]. Vertical or horizontal selection [134] is selected by signal line [153];

A signal [200] is sent from external transmitter "beamformer" electronics though I/O line [116] to the electronics associated with each tile [110]. In general, the timing of this signal is different for each tile in the array. It is dependent on the direction and focusing properties of the desired transmitted beam.

Within the integrated circuitry of each tile [110], additional time delays are added to signal [200] by Tx delay module [182]. The amount of time delay is determined by the direction of the beam desired. This will be discussed in detail below.

These time-delayed signals [160] are sent to the eight transmitters [158], which then energize strips 1 through 8 of piezoelectric transducers [18], be they in vertical or horizontal orientation, producing ultrasound signals [202], which radiate into the target medium.

Figure 17:
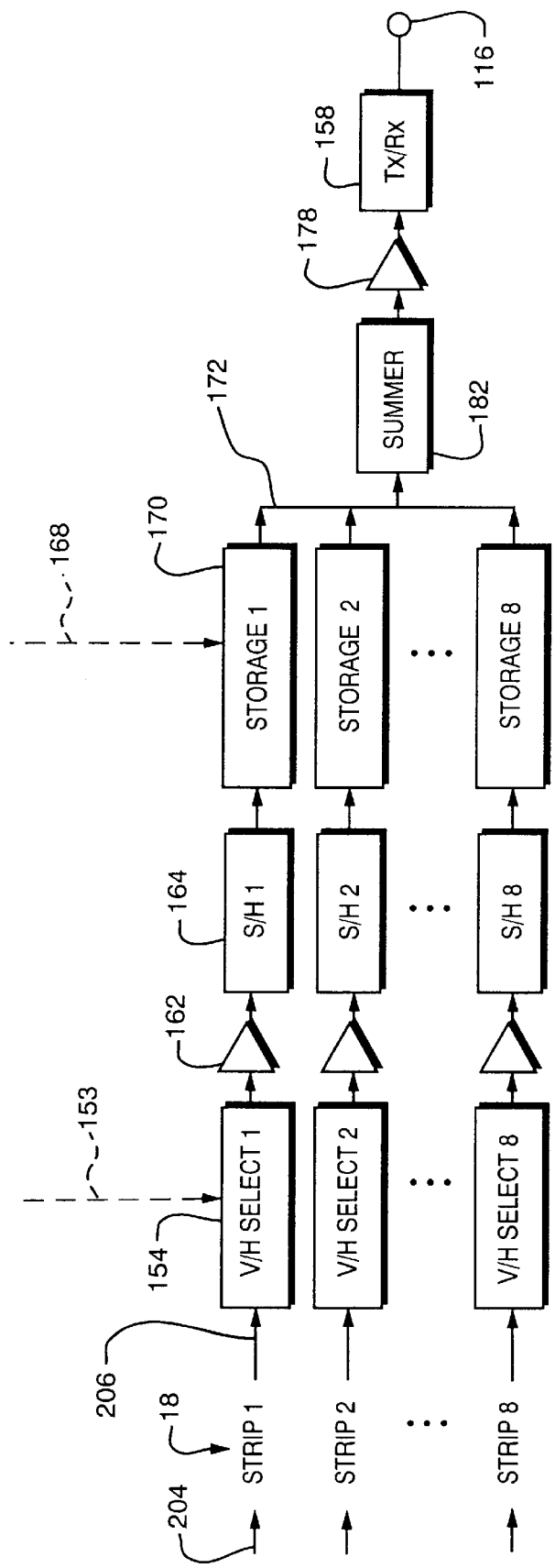
FIG. 17 is a block diagram describing the signal processing flow in a subarray of FIG. 12 in the receiving mode.

FIG. 17 describes the signal processing flow on reception, again referring to FIGS. 5–15:

All Tx/Rx switches [156], [158] are set to receive (Rx) by signal line [157]. Vertical or horizontal selection [134] is selected by signal line [153];

A continuous stream of ultrasound signals [204] reflected from the target medium is received by piezoelectric transducers [18] composing strips 1 through 8 where they are converted to electrical signals [206];

Preamplifiers [162] amplify signals [206] and drive the electronics that follow;

Sample-and-hold (S/H) electronics [164] sample these signals at a rate determined by signal processing algorithms employed.

Time delay [170] delays these samples;

The stored signals are read out with a time delay determined by the direction of the receiver beam desired and selected through signal line [168]. This will be discussed below;

The time-delayed signals from strips 1 through 8 are transmitted through signal lines [172] to receiver summer (Rx summer) [154] where they are added together;

Output amplifier [178] provides amplification and drives external electronics through switch [158] and I/O line [116].

FIG. 18A and B show the sector scanning pattern in the XZ plane with the horizontal switches selected and explains the time delay requirements on transmit or receive. Sector scanning in the YZ plane with vertical switches selected is identical in principle and will not be discussed. FIG. 18A shows an array [108] in cross-section. Acoustical medium [220] contains an acoustical scatterer [222], which is the target to be imaged. Line [224] is the axis normal to the plane of the array. Radial lines [226] and [228] are the limits of the scanning angles from the array. Arc [230] represents the lower edge of the scan.

Close up FIG. 18B shows an enlarged cross-sectional view of array [108] of FIG. 18A. Dotted line paths [174] and [178] are the paths from the edges of array [108] to target [222]. Dotted line [175] is the arc of a circle with target [222] at it center. Paths [232] and [234] are the paths from the edges of typical horizontal tile [112] or vertical tile [118]. Line [236] is the arc of a circle with target [222] at it center.

Line [238] thus represents the path difference between target [222] and the edges of the tile. This is to be compared with the much larger path difference [240] between dotted lines [174] and [178], the path distance at the edges of the entire array [108]. These path differences are related to time differences by the velocity of sound in the medium.

On transmit, the time delay required for signals from the transducer at the left edge of the tile to reach target [222] at the same time as signals from the transducer at right edge is thus determined by the time derived from path difference [238]. Similarly, the path differences between other transducers of the tile may be used to derive the time delay required between transducers.

On reception, the same time delays are required to bring signals from target [222] together at the same time due to these differences in path lengths. The relatively small time delay required by path difference [238] compared to the larger path difference [240] of the entire array minimizes the number of samples required in the time delay module [170] and the length of the time delay required.

Figure 19:
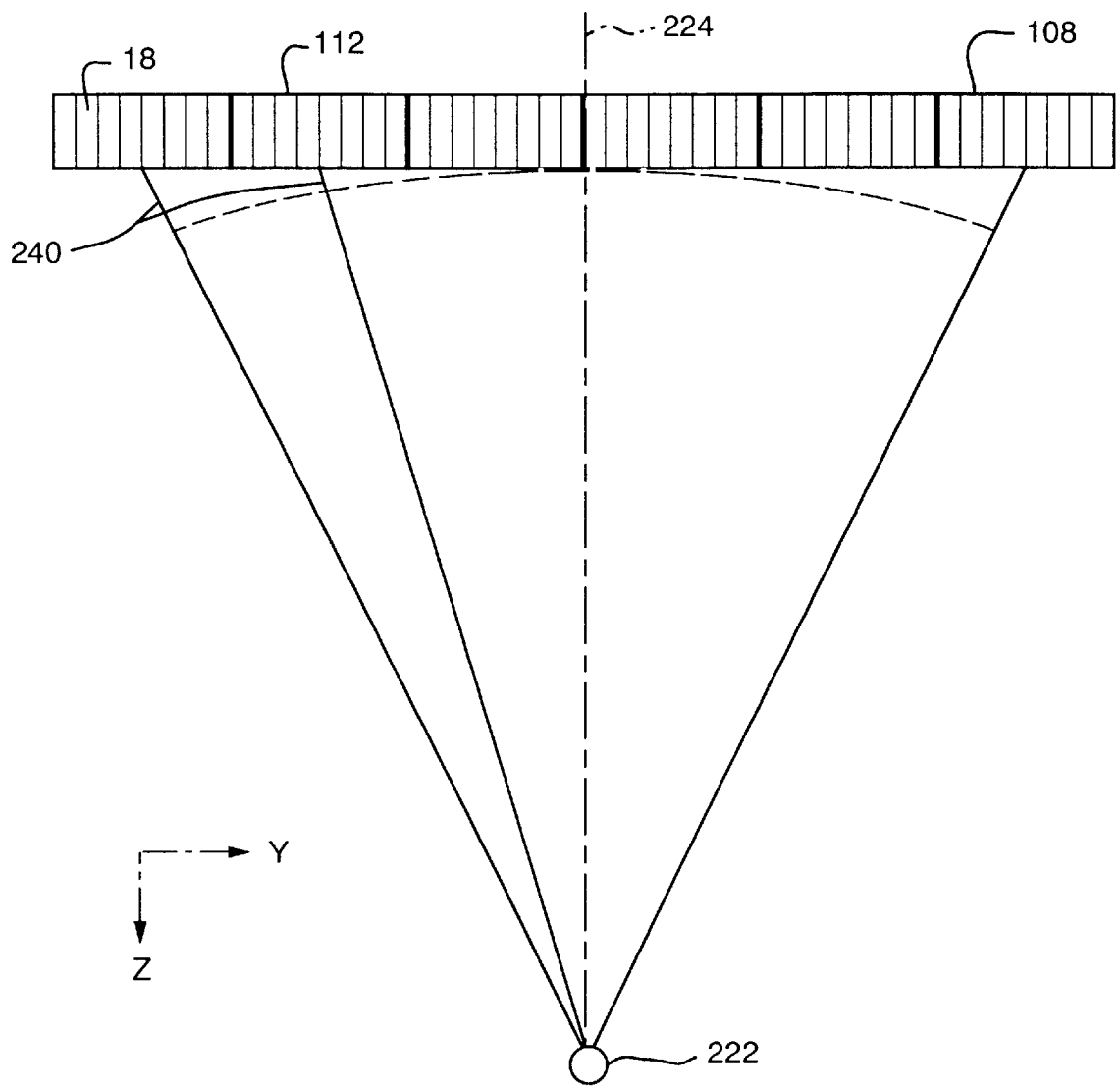
FIG. 19 is a cross section view of the array from a beam focusing perspective, illustrating the relative path length between subarrays.

FIG. 19, again also referring to FIGS. 5–15, shows beam focusing in the YZ plane with the horizontal switches selected. In this case, transducers [18] are electrically connected together to effectively form a single large strip [112] of transducers. There are thus no time delays in this dimension within strip [112]. Instead, any time delays between multiple strips due to path differences [240] are derived from the system console electronics sent over cable [322] containing signal lines [116]. These external time delays may be used in the YZ plane to provide beam focusing on-axis as a 1.5 D array or focusing and limited angle scanning (not shown) as a 1.75 D array.

Figure 20:
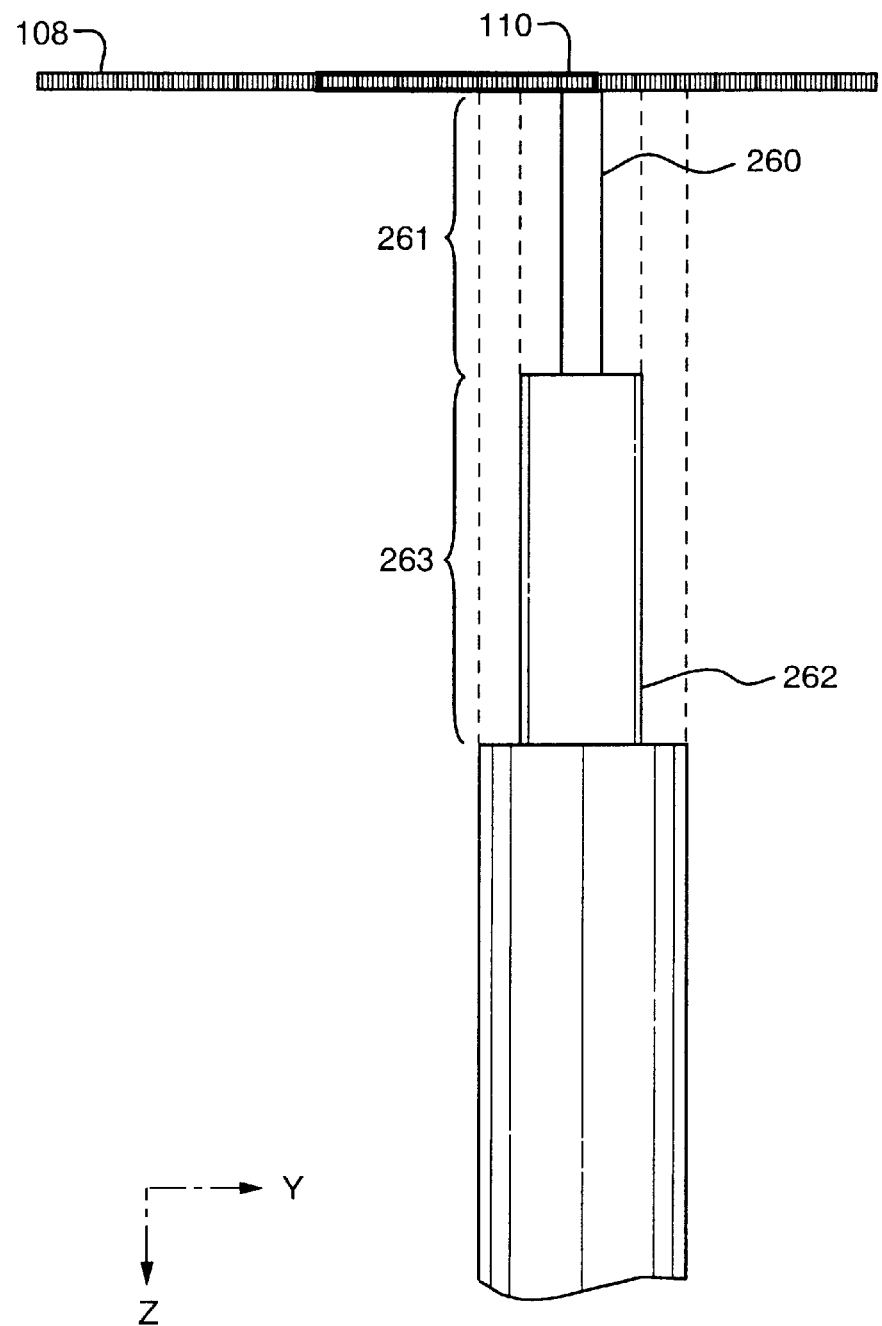
FIG. 20 is a cross section diagram illustrating an expanding aperture scan using a matrix array.
Figure 21:
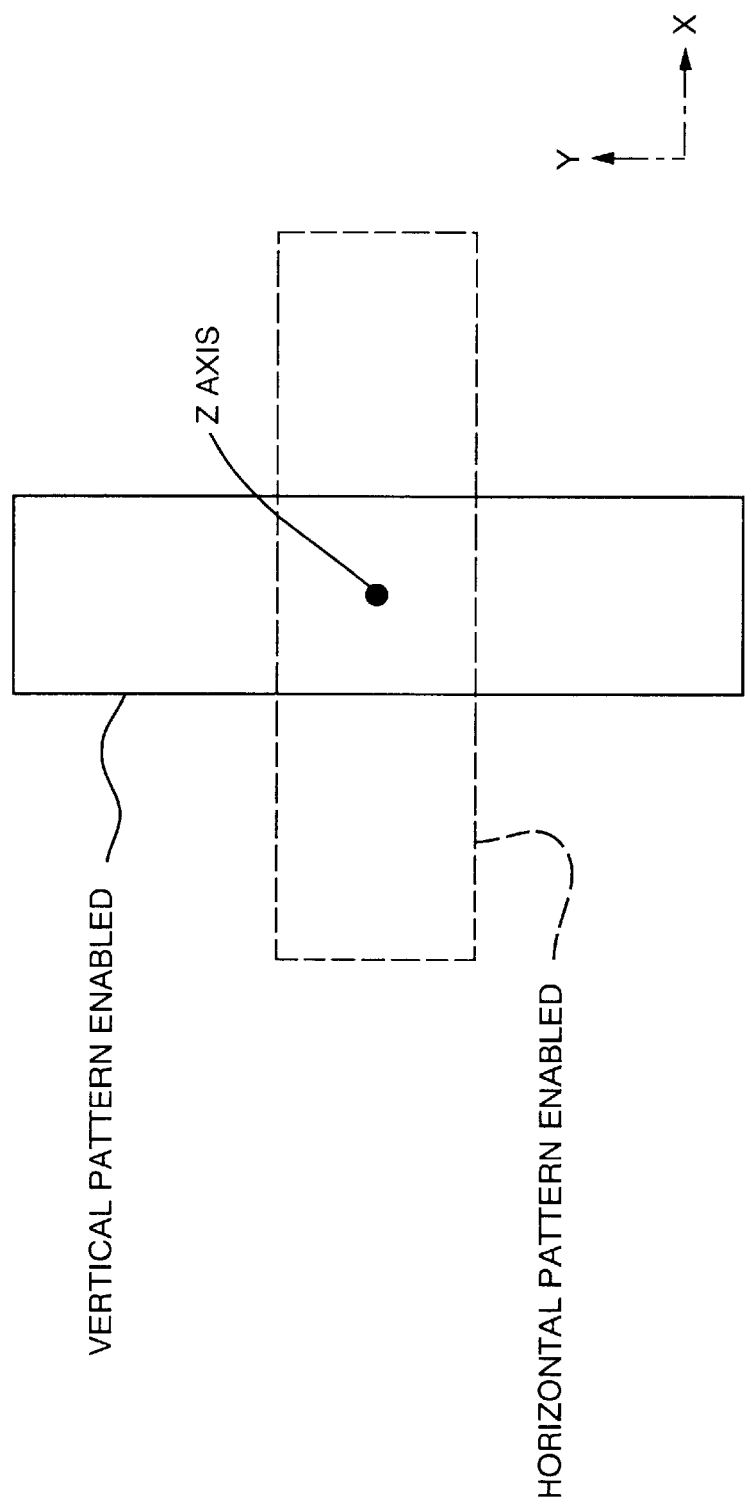
FIG. 21 is a Z axis diagrammatic view illustrating the selectable configurations of the array as between vertical and horizontal operating modes.

FIGS. 20 and 21 show how this array may be used to scan over a large volume of the acoustical medium. FIG. 20 shows an "expanding aperture scan" in the YZ plane in the manner of a 1.25 D array using techniques well known in the ultrasound imaging art. For a short period, only one tile [110] is used to transmit and receive. This results in a narrow beam profile [260]. This narrow beam profile only exists for a short z distance due to beam spreading. This distance $z_1 \cong a^2/4\lambda$ where a is the width of the tile and $\lambda$ is the wavelength of the ultrasound. Received signals from the array face to $z_1$[261] are used in the image. Signals beyond this $z_1$ range are not used.

On the next transmit/receive cycle, three adjacent tiles [110] are active resulting in beam pattern [262]. Received signals from the range $z_2$–$z_1$[263] are used in the image. This may repeated by adding additional tiles until the total number of tiles available is used. As more tiles are added to the beam, time delays may be introduced between the tiles to provide a focusing effect as in the 1.5 D array example of FIG. 19.

Sector scanning over a limited angle in the YZ plane may also be realized with the time delays sent to the separate tiles from the console. The maximum scanning angle is limited to avoid grating lobes, which introduce artifacts into the image. These grating lobes, which are a function of the lateral dimensions of the tiles and the ultrasound frequency, are well known to those experienced in the ultrasound scanning art.

FIG. 21 depicts the total angular pattern that may be achieved with the two switched configurations of the array. Combinations of scanning, focusing and expanding aperture are used to produce a high-resolution scanning pattern. By thus gathering data from a volume, a three-dimensional image of the structures in the body may be rendered by techniques well known in the ultrasound imaging art.

Scanning planes at right angles to each other may be rapidly selected electronically by choosing either the vertical or horizontal tile transducer array configurations. This has important advantages when imaging a three-dimensional target such as a tumor to determine its volume or an artery to determine blood flow volume. Rapidly in this context includes "real-time" electronic switching, or faster than the human eye can detect in the order of 12 to 30 times per second or faster, well within the capability of contemporary electronic circuits. It is also possible to switch between scanning planes on a line-by-line basis rather than completing an entire scan before starting the next one. This reduces image motion artifacts.

An additional and very important advantage of this invention is the ability to perform "aberration correction". Aberrations arise from the sound pulse traversing the structures inside the body. These structures generally have differing velocities of sound as well as complex spatial distributions.

Figure 22:
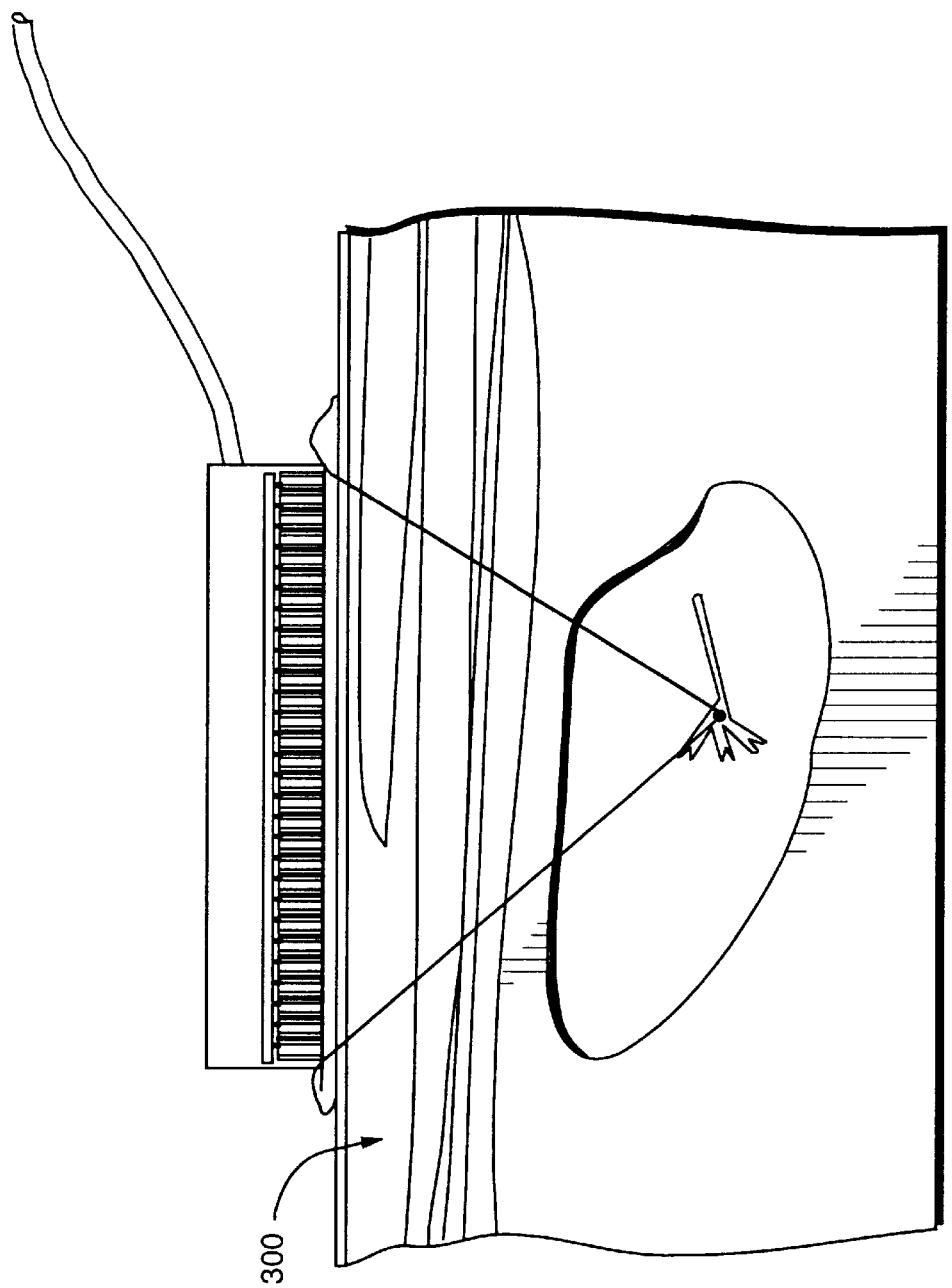
FIG. 22 is a cross section illustration of a probe aligned over a target medium of irregular signal propagation characteristics, for imaging an object within.

For example, referring to FIG. 22, imaging inside the human abdomen with an external probe requires traversing the abdominal wall with the ultrasound beam. Anatomical structures such as muscle fascia, fat deposits and abdominal ligaments have different velocities of sound propagation (Table II.) In obese patients, who have a large fat content in their abdominal walls, these variations are well known to lead to poorer image quality than in patients with muscular abdominal walls.

TABLE II

Velocity of Sound in Selected Human Tissue

| Tissue Type | Velocity of Sound- meter/sec |
|---|---|
| Abdominal Muscle | 1585 |
| Abdominal fat | 1450 |
| Liver parenchyma | 1549 |
| Average value of human tissue | 1540 |

Ultrasound imaging systems conventionally use the average velocity of sound and assume it is constant throughout the scanning region. Variations of time delays and amplitude changes through the abdominal wall lead to errors in the scanning and focusing of ultrasound signals from arrays. In a conventional linear array, with time delays in only one dimension, errors in the out-of-plane dimension cannot be compensated.

These variations tend to vary somewhat slowly over the array aperture. An "isoplanatic patch" or area over which the time delay and amplitude errors are correlated, as been measured to be about 1.5 mm×1.5 mm at 3.5 MHz. Correction of the time delays and amplitudes is not required on a smaller area. With one embodiment of this invention, the size of a tile may be selected to approximate the dimensions of the "isoplanatic patch" at the frequency of interest. Time delay and amplitude corrections may then be introduced for each tile from the ultrasound console [270] to compensate for the aberrations, producing greatly improved image quality.

During an examination, when the probe is manually moved over the patient, these aberrations may be corrected by adaptively adjusting the time delays and amplitude at each channel of an ultrasound array.

It will be readily apparent that more sophistication can be incorporated into the matrix. For example, a matrix with excess subarrays properly configured can provide for selective lateral positioning of the functional array, vertical or horizontal or both. This offers possible reconfiguration schemes that permit mapping out substandard transducers or subarrays.

Another preferred embodiment recognizes that the subarrays within the matrix can be divided between those in the overlapping area which must be switchable between horizontal and vertical busses and modes of operation, and those in the "wings" or the vertically or horizontally extending regions that need only operate in one mode or the other. Economies of scale and common components suggest that the subarrays be all the same, but there are considerations of power and simplified circuitry that may in some cases be significant.

Figure 23:
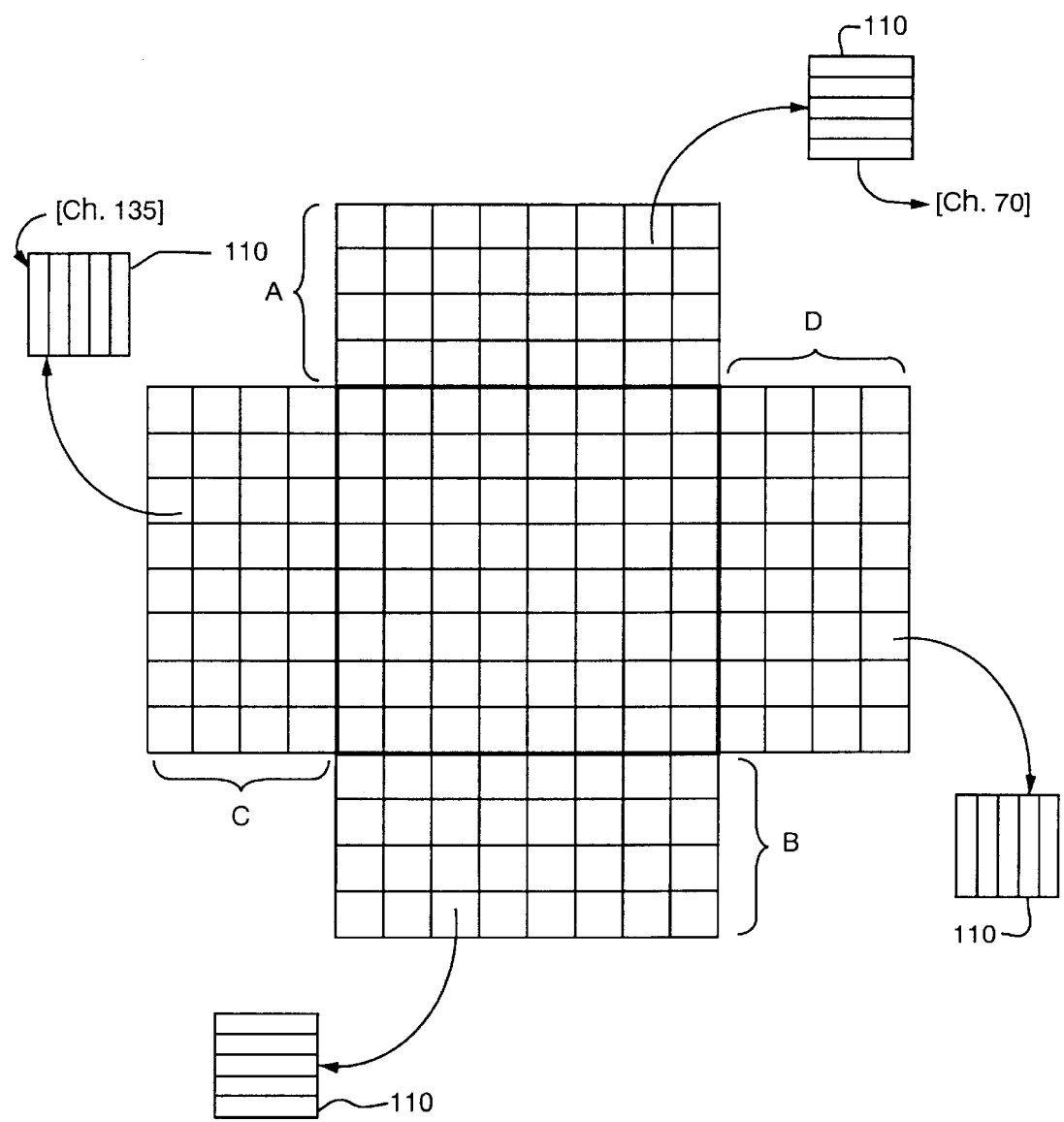
FIG. 23 is a matrix array of another embodiment of the invention, having 192 subarrays where four outboard regions of either vertical or horizontal subarray orientation flank a center region of subarrays that are switchable between vertical and horizontal orientations.

Referring to FIG. 23, an 8 by 16 vertical configuration of subarrays overlapping an 8 by 16 horizontal configuration of subarrays yields a matrix array of 192 tiled subarrays, divided into five regions, the 8 by 8 center region with 64 subarrays and signal lines being flanked by four 4×8 regions designated A, B, C, and D, each having 32 subarrays and signal lines. The subarrays or tiles [110] of regions A and B need operate only in the horizontal mode, while regions C and D may be confined to vertical mode operation, orthogonal to the A and B regions, as illustrated by the enlarged exemplary tile [110] from each region. As is readily apparent, only 128 subarrays are active at one time, 64 from the center region switch selected for either a vertical or horizontal orientation, and 32×2 from the likewise oriented two of the flanking regions.

However, where subarrays are available in both switchable and fixed orientations and configured as described, the system circuitry and connector capacity can be optimized for either of two useful conditions. The system design can provide 192 signal channels in the cable or other transmission medium, with a 64 line switching capability as between regions A, B and C D subarrays, located at the interface box or system end of the cable. Alternatively, the system can be limited to only 128 signal channels in the cable or transmission medium, with the switching capability for switching between vertical and horizontal regions located in the probe end of the cable, preferably in the integrated circuitry proximate the matrix array.

It is understood that in this variant of the invention, the subarrays in the overlapping or center region must be operable in either orientation and switchable, preferably in real-time, as previously described. Depending on the pattern selected for the transducer array fabrication, the overlapping region could be at the ends of the vertical and/or the horizontal subarray patterns, yielding an L or a T configuration with two or three flanking regions rather than the four described for the cross pattern. These cases will have a different switching assignment as between the vertical and horizontal subarrays of the flanking regions, in order to keep the proper orientation in both vertical and horizontal modes. In all cases there will be at least two orthogonally oriented flanking regions, the subarrays of each configured and operating in only one of the two modes, as vertical linear strip arrays or as horizontal linear strip arrays.

Figure 24:
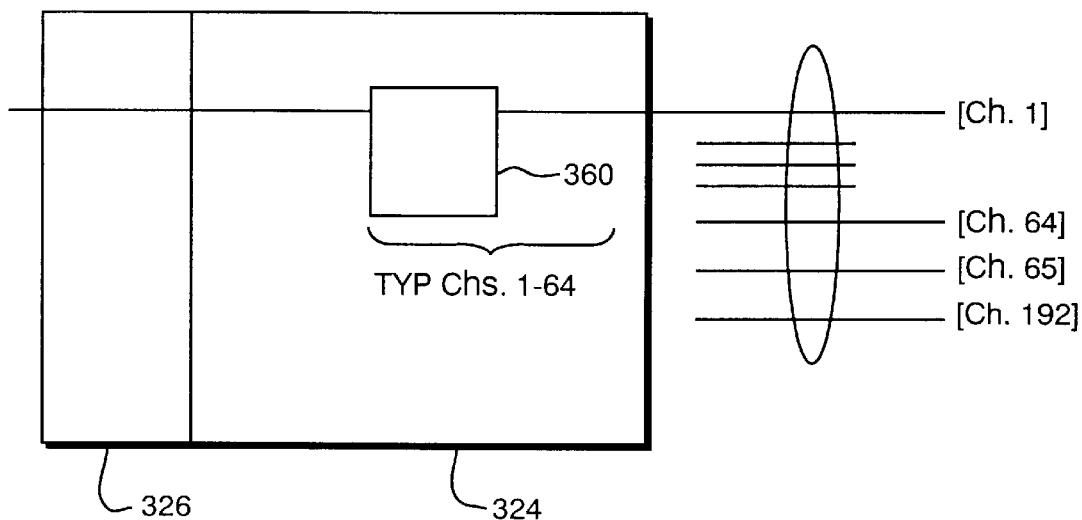
FIG. 24 is partial cross section diagram of another embodiment of an interface box having 192 signal channels.
Figure 25:
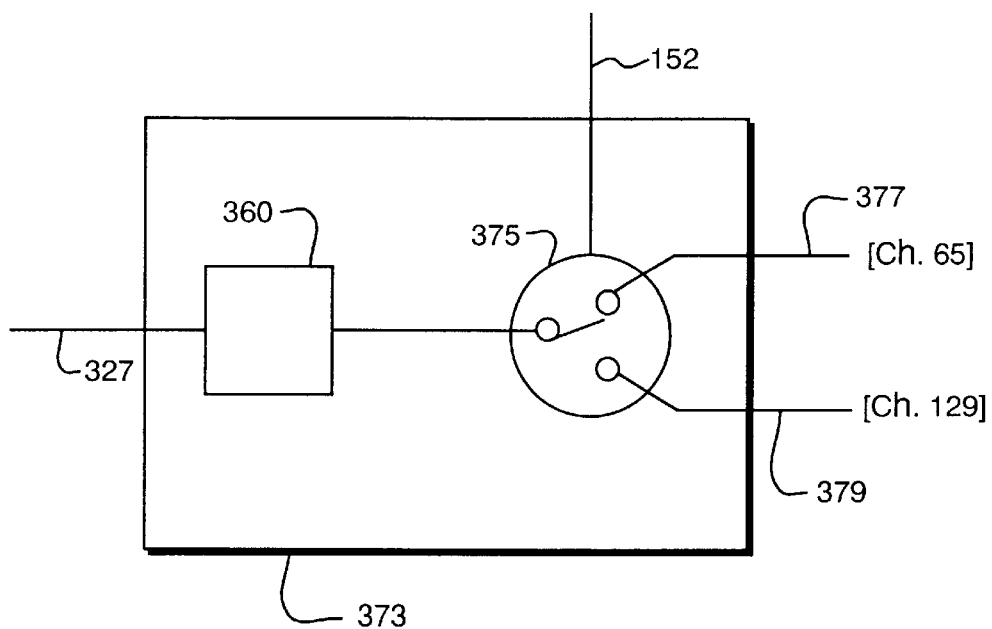
FIG. 25 is a block diagram of a Vertical/Horizontal, channel/subarray selector switch of the interface box of FIG. 24.

Referring to FIGS. 24 and 25, and also referring back to FIGS. 5–15 and 23 for context, there is illustrated the case where there are 192 signal channels in the cable or transmission medium, with the host system end or interface box configured for switching as between the vertical 64 and the horizontal 64 of the 128 channels connected to the respective flank regions of the cross pattern of FIG. 23. Interface box [324] contains 192 signal lines connecting to the probe. T/R switch and amplifier circuits [360] on channels 1–64 are dedicated to the center region of the matrix array.

Referring to FIG. 25, channels 65 through 128 must be switched one to one with corresponding channels 129 through 192; e. g. for orthogonal switching of the probe between vertical and horizontal operation, channel 70 and channel 134 must be switchable at the interface box [374] or host end of the system. To provide for this capability, channel selector [373] incorporates a switch and amplifier [360] with a T/R switch [375], which is controlled by V/H control line [152], originating at controller [332]. Switch [375] selects between a vertically oriented subarray in region A and a horizontally oriented subarray in adjacent region C. In this example, subarray [70]corresponding to channel 70 is paired for switching with subarray [135] corresponding to channel 135. The other subarrays of the flanking regions are likewise switched at the same time.

The alternate configuration and circuitry for using 128 signal lines in the cable to service 192 subarrays, requires using probe end switches for switching 64 of those lines as between the vertical and horizontal flanking regions of subarrays. The circuitry required for this configuration will be readily apparent to those skilled in the art from the above description, is clearly within the scope of the invention, and need not be described further.

There are numerous other embodiments within the scope of the invention. For example, there is an orthogonally switchable matrix array transducer for ultrasound imaging, consisting of a multiplicity of tiled planar acoustic/electronic subarrays, each subarray consisting of an N vertical by N horizontal pattern of uniformly spaced acoustical transducers fabricated on a transducer substrate and closely connected to supporting circuitry, such as a CMOS integrated circuit in a supporting substrate which is flip chip mounted and bump bonded for electrical contacts to the acoustical transducer or transducer array chip.

N may be at least 2 transducers and is preferably 8 transducers, yielding a preferred subarray of 8 by 8 transducers. The supporting circuitry may include N vertical and N horizontal bus lines and transducer switches connected to each transducer, N transducers being connected to each vertical and each horizontal bus line, where each of the transducers has a connection that can be switched to its respective vertical or its horizontal bus line. All of the transducer switches are controlled by a bus selector switch and control signal so as to enable reconfiguration of the subarray between a set of N vertical linear transducer strips for vertical mode operation and a set of N horizontal linear transducer strips for horizontal mode operation.

Alternatively, some subarrays and supporting circuitry may be limited to either vertical or horizontal bus lines, without need for a switching capability, so that those subarrays are operable only in one configuration or the other. A common subarray chip configuration limited to a single orientation of linear transducer strip arrays can be rotated for assembly as either a vertical or horizontal component of the matrix array.

The supporting circuitry of a subarray may further include a transmit/receive selector switch controlled by a signal line enabling the subarray to be switched between a transmit and a receiving mode, a linear transducer strip transmitter time delay circuit enabling the linear transducer strips to be relatively time shifted for transmitting, a receiver time delay circuit enabling the linear transducer strips to be time shifted for receiving. There may be summer circuit for integrating the received signals of all the linear transducer strips of the subarray into a common output signal.

The supporting circuitry may yet further include means such as a wire or optical multi-conductor cable, or a wireless data transmission scheme in combination with separate power lines or batteries, for connecting the subarrays to a host control system. The connections must provide power and control inputs to each subarray of the matrix array transducer for transmit steering, receive steering, selecting between vertical and horizontal operation, power, and clock signals if needed. The host control system would thereby also be accepting the output signals from the summer circuits of each respective subarray.

The supporting circuitry may be being switchable in real-time between respective vertical and horizontal bus lines to enable real-time reconfiguration of the matrix array between vertical and horizontal modes of operation.

The multiplicity of tiled subarrays that make up the full matrix array may be configured as a pair of W subarray wide by L subarray long, orthogonally oriented arrays, whether overlapping or not, where W is at least 1 and preferably at least 5 subarrays wide, and L is at least 8 and preferably at least 128 subarrays long. Where the orthogonal arrays are overlapping, they share common subarrays at the area of overlap.

There may be an orthogonally switchable matrix array transducer according to the invention, combined with a multiconductor cable and an interface box attachable to a host control system, which may include a portable computer system and suitable software. Alternatively, the host control system may be a portable or non-portable general purpose computer system and suitable software and an interface box, where the interface box includes a beam former control capability compatible with the matrix array of the probe.

Yet another example of the invention is an orthogonally switchable matrix array transducer of the general N×N transducer with supporting circuitry construction described above, where the vertical and horizontal array patterns are overlapping and sharing common subarrays at the area of overlap, but where the remaining subarrays consist of two flanking regions of fixed mode subarrays. There is a first flanking region of subarrays in which the supporting circuitry includes N vertical bus lines, each transducer is connected to a vertical bus line, N transducers to each vertical bus line, so that the subarray functions as a set of N vertical linear transducer strips for vertical mode operation. There is a second flanking region of subarrays in which the supporting circuitry includes N horizontal bus lines, each transducer connected to a horizontal bus line, N transducers to each horizontal bus line, so that each of these subarrays functions as a set of N horizontal linear transducer strips for horizontal mode operation.

This embodiment may have supporting circuitry in the form of an integrated circuit fabricated on a circuit substrate which is bonded to the transducer substrate so as to provide electrical connections to the transducers, and where the supporting circuitry in the overlapping area of common subarrays is switchable in real-time between vertical and horizontal bus lines and operation so as to enable real-time reconfiguration of the probe between vertical and horizontal modes of operation, while the fixed mode subarrays in the flanking regions need be selectable in real-time only as between the first flanking region and the second flanking region in order to complete the scan pattern.

As another example of the invention, there is a method for performing ultrasound imaging consisting of the following steps:

(a) Using a matrix array transducer probe remotely connected to a control system, where the transducer probe consists of a multiplicity of tiled subarrays of N by N transducers, where the subarrays are oriented in a pattern having a vertical component overlapping a horizontal component, and where the subarrays are selectable as either the vertical component combination or the horizontal component combination of subarrays. Each subarray is switchable between a first operating mode of horizontal linear transducer strip arrays and a second operating mode of vertical linear strip arrays, the output of the linear strip arrays of each tiled subarray being summable by supporting circuitry within the transducer probe as a single output signal, N being equal or greater than 2, and the output signals being communicated to the control system.

(b) Command and record a first ultrasound image in the first mode;

(c) Switch the transducer probe operation between the first mode and the second mode; and (d) Command and record a second ultrasound image in the second mode.

There may be a further step:

(e) Integrate the first ultrasound image with the second ultrasound image so as emulate two-dimensional ultrasound operation, and produce real-time, three-dimensional imagery.

As still yet another example, there is a method for performing ultrasound imaging consisting of the steps:

(a) First, use a matrix array transducer probe remotely connected to a control system, where the transducer probe consists of a multiplicity of tiled subarrays of N by N transducers, with the subarrays oriented in a pattern having a vertical component and a horizontal component with an area of overlap. There is a first flanking region associated with the vertical component of the pattern, and a second flanking region associated with the horizontal component. The subarrays of the first flanking region are configured as N horizontal linear strip arrays, and the subarrays of the second flanking region are configured as N vertical strip arrays. The subarrays of the flanking regions selectable in real-time between first and second flanking region, while the subarrays in the area of overlap are bi-modal subarrays switchable between a first operating mode of horizontal linear transducer strip arrays and a second operating mode of vertical linear strip arrays, the output of said linear strip arrays of each said subarray being summable by supporting circuitry within the transducer probe as a single output signal, N being equal or greater than 2. The dual switching capability permits real-time cross axis operation of the scanner system, emulating a full two dimensional scanner capability with fewer transducers and fewer cable conductors than would otherwise be required. The output signals are communicable to said control system.

(b) Command and record a first ultrasound image in the first operating mode.

(c) Switch between flanking region subarrays, and switch the orientation of the subarrays in the overlapping area between the first operating mode and the second operating mode.

(d) Command and record a second ultrasound image in the second mode.

The steps of switching between modes may occur in real-time, so as to permit real-time imaging or imaging at the same speed as recorded so as to emulate a full two dimension array scanning capability, and to thus enable a real-time, three dimensional presentation to human viewers. It will be appreciated by those skilled in the art, that the switching as between orthogonally modes can be executed on a frame by frame basis, with X and Y axis computations being executed concurrently in separate circuitry, and then be integrated into a three dimensional presentation. Alternately, any useful number of frames may be executed in one dimension or axis at a time, sufficient for a set of computations in that axis, then switching the array and the computing circuitry to the orthogonal axis for a similar subroutine. The results may then be compiled for the 3D presentation.

The invention is susceptible to other and various embodiments within the scope of the appended claims, as will be readily evident to those skilled in the art from the description and figures provided.

What is claimed is:

1. An orthogonally switchable matrix array transducer system for ultrasound imaging, comprising:
   a multiplicity of subarrays of N by N transducers, where N is at least 2;
   a bus including N vertical bus lines and N horizontal bus lines, where each of the transducers of at least one subarray is switchably connected to a vertical bus line and to a horizontal bus line, thereby enabling reconfiguration of the at least one subarray between a horizontal mode of operation and a vertical mode of operation; and
   a summer circuit adapted for integrating signals output by one or more of the subarrays into a common output signal that can be processed by a control system.

2. The system of claim 1 further comprising:
a bus selector that is adapted to control switching of the transducers between respective vertical and horizontal bus lines.

3. The system of claim 1 wherein the transducers are switched between respective vertical and horizontal bus lines in real-time so as to enable real-time reconfiguration between the horizontal and vertical modes of operation.

4. The system of claim 1 wherein the subarrays are electrically coupled to the control system by at least one of a wireless data transmission scheme and a multiconductor cable.

5. The system of claim 1 further comprising:
a transmit/receive selector switch configured to switch each subarray between a transmit and a receiving mode.

6. The system of claim 1 wherein a number of the subarrays are configured and operated as a vertical linear array or a horizontal linear array, and the system further includes:
a transmitter time delay circuit adapted for enabling transducers of either linear array to be time shifted for transmitting; and
a receiver time delay circuit adapted for enabling transducers of either linear array to be time shifted for receiving.

7. The system of claim 1 wherein the control system provides control inputs to each subarray to enable at least one of transmit steering, receive steering, selecting between vertical and horizontal operation, power, and clock signals.

8. The system of claim 1 wherein the control system includes a processor and an interface box, the interface box configured with beam former control capability.

9. The system of claim 1 wherein the multiplicity of subarrays are configured as a pair of orthogonally oriented arrays.

10. The system of claim 9 wherein the multiplicity of subarrays include an area of overlap.

11. The system of claim 10 further comprising:
a first flanking region of subarrays not included in the overlap area, with each transducer in the first flanking region connected to a vertical bus line, the first flanking region subarrays adapted to function as a set of N vertical linear arrays for horizontal mode operation; and
a second flanking region of subarrays not included in the overlap area, with each transducer in the second flanking region connected to a horizontal bus line, the second flanking region subarrays adapted to function as a set of N horizontal linear arrays for vertical mode operation.

12. The system of claim 11 wherein the subarrays in the overlap area are switchable in real-time as between respective vertical and horizontal bus lines so as to enable real-time reconfiguration between the horizontal and vertical modes of operation, and the subarrays in the flanking regions are selectable in real-time as between the first flanking region and the second flanking region so as to enable scan pattern completion.

13. A method for performing ultrasound imaging with a matrix array transducer probe, the transducer probe including a multiplicity of tiled subarrays of transducers, the subarrays oriented in a pattern having a vertical component overlapping a horizontal component, wherein at least one of the subarrays is switchable between a horizontal operating mode and a vertical operating mode, and output signals of the tiled subarrays can be integrated into an output signal, the method comprising:
recording one or more ultrasound images in the horizontal operating mode;
switching between the horizontal operating mode and the vertical operating mode; and
recording one or more ultrasound images in the vertical operating mode.

14. The method of claim 13 further comprising:
integrating the ultrasound images recorded in the horizontal operating mode with the ultrasound images recorded in the vertical operating mode so as to generate real-time, three dimensional ultrasound imagery.

15. The method of claim 13 wherein switching between the modes includes switching in real-time.

16. An orthogonally switchable matrix array transducer system, comprising:
a multiplicity of subarrays of transducers configured as orthogonally oriented arrays that include an area of overlap;
a bus including vertical bus lines and horizontal bus lines, where each of the transducers of at least one subarray is switchably connected to a vertical bus line and to a horizontal bus line, thereby enabling real-time reconfiguration of the at least one subarray between a horizontal mode of operation and a vertical mode of operation; and
a summer circuit adapted for integrating signals output by one or more of the subarrays into a common output signal.

17. The system of claim 16 further comprising:
a bus selector that is adapted to control switching of the transducers between respective vertical and horizontal bus lines; and
a transmit/receive selector switch configured to switch each subarray between a transmit and a receiving mode.

18. The system of claim 16 wherein a number of the subarrays are configured and operated as a vertical linear array or a horizontal linear array, and the system further includes:
a transmitter time delay circuit adapted for enabling transducers of either linear array to be time shifted for transmitting; and
a receiver time delay circuit adapted for enabling transducers of either linear array to be time shifted for receiving.

19. The system of claim 16 further comprising:
a first flanking region of subarrays not included in the overlap area, with each transducer in the first flanking region connected to a vertical bus line, the first flanking region subarrays adapted to function as a set of N vertical linear arrays for horizontal mode operation; and
a second flanking region of subarrays not included in the overlap area, with each transducer in the second flanking region connected to a horizontal bus line, the second flanking region subarrays adapted to function as a set of N horizontal linear arrays for vertical mode operation.

20. The system of claim 19 wherein the subarrays in the overlap area are switchable in real-time between respective vertical and horizontal bus lines so as to enable real-time reconfiguration between the horizontal and vertical modes of operation, and the subarrays in the flanking regions are selectable in real-time as between the first flanking region and the second flanking region so as to enable scan pattern completion.

* * * * *